US011840707B2

United States Patent
Rhainds et al.

(10) Patent No.: US 11,840,707 B2
(45) Date of Patent: Dec. 12, 2023

(54) CO-CULTURE SYSTEM AND METHOD FOR IN VITRO ASSESSMENT OF REVERSE CHOLESTEROL TRANSPORT

(71) Applicant: INSTITUT DE CARDIOLOGIE DE MONTREAL, Montreal (CA)

(72) Inventors: David Rhainds, Montréal (CA); Éric Rhéaume, Montréal (CA); David Busseuil, Montréal (CA); Jean-Claude Tardif, Laval (CA)

(73) Assignee: INSTITUT DE CARDIOLOGIE DE MONTREAL, Montreal (CA)

( * ) Notice: Subject to any disclaimer, the term of this patent is extended or adjusted under 35 U.S.C. 154(b) by 357 days.

(21) Appl. No.: 16/301,494

(22) PCT Filed: May 30, 2017

(86) PCT No.: PCT/IB2017/053172
§ 371 (c)(1),
(2) Date: Nov. 14, 2018

(87) PCT Pub. No.: WO2017/208149
PCT Pub. Date: Dec. 7, 2017

(65) Prior Publication Data
US 2019/0284527 A1 Sep. 19, 2019

Related U.S. Application Data

(60) Provisional application No. 62/343,388, filed on May 31, 2016.

(51) Int. Cl.
| | | |
|---|---|---|
| *C12N 5/071* | (2010.01) | |
| *C12M 3/06* | (2006.01) | |
| *C12M 1/04* | (2006.01) | |
| *C12M 1/00* | (2006.01) | |
| *C12N 5/0786* | (2010.01) | |
| *C12N 5/074* | (2010.01) | |
| *C12Q 1/60* | (2006.01) | |
| *C12M 1/34* | (2006.01) | |
| *G01N 33/92* | (2006.01) | |
| *C12M 3/00* | (2006.01) | |

(52) U.S. Cl.
CPC .............. *C12N 5/067* (2013.01); *C12M 1/34* (2013.01); *C12M 3/00* (2013.01); *C12M 23/16* (2013.01); *C12M 23/24* (2013.01); *C12M 23/34* (2013.01); *C12N 5/0645* (2013.01); *C12N 5/0696* (2013.01); *C12Q 1/60* (2013.01); *G01N 33/92* (2013.01); *C12N 2502/1157* (2013.01); *C12N 2502/14* (2013.01); *C12N 2503/02* (2013.01)

(58) Field of Classification Search
CPC ..... G01N 33/92; G01N 33/5055; C12N 5/067
See application file for complete search history.

(56) References Cited

U.S. PATENT DOCUMENTS

| | | | |
|---|---|---|---|
| 2006/0166891 A1 | 7/2006 | Sircar et al. | |
| 2011/0152112 A1 | 6/2011 | Johansson | |
| 2015/0316566 A1* | 11/2015 | Dasseux | ............ G01N 33/5088 514/7.4 |

FOREIGN PATENT DOCUMENTS

| | | |
|---|---|---|
| WO | WO-2004/028546 A1 | 4/2004 |
| WO | WO-2004/094471 A2 | 11/2004 |
| WO | WO-2006/049597 A1 | 5/2006 |
| WO | WO-2009/155366 A2 | 12/2009 |

OTHER PUBLICATIONS

Bie et al., "Macrophage-specific transgenic expression of cholesteryl ester hydrolase attenuates hepatic lipid accumulation and also improves glucose tolerance in ob/ob mice", American Journal of Physiology, Endocrinology and Metabolism, 2012, 302(10): E1283-E1291. (Year: 2012).*
Wu et al., "Suppression of hepatocyte CYP1A2 expression by Kupffer cells via AhR pathway: The central role of proinflammatory cytokines", International Journal of Molecular Medicine, 2006, vol. 18, pp. 339-346. (Year: 2006).*
Sezgin et al., "A comparative study on fluorescent cholesterol analogs as versatile cellular reporters", Journal of Lipid Research, 2016, vol. 57, pp. 299-309. (Year: 2016).*
Gaibelet et al., "Specific Cellular Incorporation of a Pyrene[1]Labelled Cholesterol: Lipoprotein-Mediated Delivery toward Ordered Intracellular Membranes", PLOS ONE, 2015, 10(4), pp. 1-27. (Year: 2015).*
Sengupta et al., "Novel technique for generating macrophage foam cells for in vitro reverse cholesterol transport studies", Journal of Lipid Research, 2013, vol. 54, pp. 3358-3372. (Year: 2013).*
Yvan-Charvet et al., "The role of HDL, ABCA1 and ABCG1 transporters in cholesterol efflux and immune responses", Arteriosclerosis, Thrombosis, and Vascular Biology, 2010, vol. 30, pp. 1-10. (Year: 2010).*
Rose et al., "Co-culture of Hepatocytes and Kupffer Cells as an In Vitro Model of Inflammation and Drug-Induced Hepatotoxicity", Journal of Pharmaceutical Sciences, published Feb. 2016, vol. 105, pp. 950-964. (Year: 2016).*
De Bittencourt et al., "Transfer of cholesterol from macrophages to lymphocytes in culture," Biochem Mol Biol Int. 44(2):347-62 (1998).
Low et al., "Cholesterol efflux assay," J Vis Exp. 61:e3810 (2012) (5 pages).
International Search Report for International Application No. PCT/IB2017/053172, dated Aug. 28, 2017 (4 pages).
Written Opinion of the International Searching Authority for International Application No. PCT/IB2017/053172, dated Aug. 28, 2017 (5 pages).

(Continued)

*Primary Examiner* — Laura Schuberg
(74) *Attorney, Agent, or Firm* — Clark & Elbing LLP

(57) ABSTRACT

The present invention provides a co-culture system and method for assessing cellular cholesterol (Choi) efflux and uptake in vitro. The co-culture system mimics in vivo Choi efflux and uptake in the context of mammalian physiology. The methods and systems provided can be used in some embodiments to evaluate the effect of a pharmacological agent on cellular Choi efflux and uptake or for diagnostic purposes.

18 Claims, 14 Drawing Sheets

(56) References Cited

OTHER PUBLICATIONS

International Preliminary Report on Patentability for International Application No. PCT/IB2017/053172, dated Dec. 4, 2018 (6 pages).
Extended European Search Report for European Patent Application No. 17805976.2, dated Dec. 6, 2019 (12 pages).
Carling, Roberta-Daila, "Utilisation d'un modele de co-culture cellulaire pour revaluation in vitro du transport inverse du cholesterol," Maitrise ès sciences, Sciences biomédicales, Universite de Montreal, Nov. 2012 (265 pages) (No English language translation provided).
Weinert et al., "The lysosomal transfer of LDL/cholesterol from macrophages into vascular smooth muscle cells induces their phenotypic alteration," Cardiovasc Res. 97(3):544-552 (2013).
Communication pursuant to Article 94(3) EPC in European Patent Application No. 17805976.2 dated Sep. 13, 2021 (5 pages).
Office Action for Canadian Patent Application No. 3,026,037 dated May 31, 2023 (6 pages).
Poirier et al., "The epigenetic drug 5-azacytidine interferes with cholesterol and lipid metabolism," J Biol Chem. 289(27):18736-51 (Jul. 2014).

\* cited by examiner

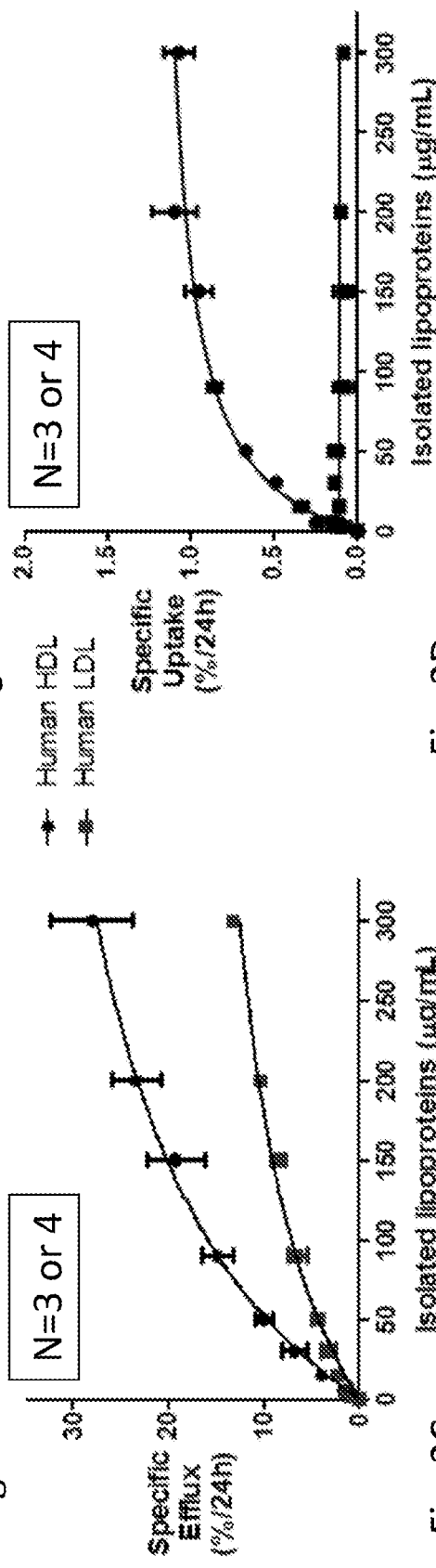
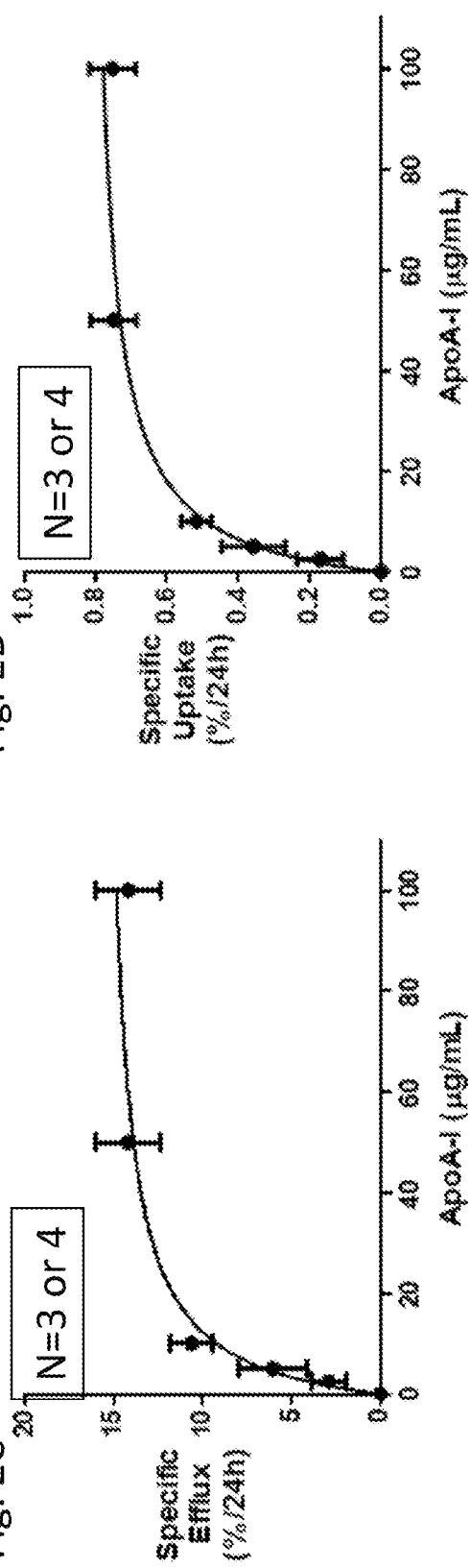
Fig. 2A  Fig. 2B  Fig. 2C  Fig. 2D

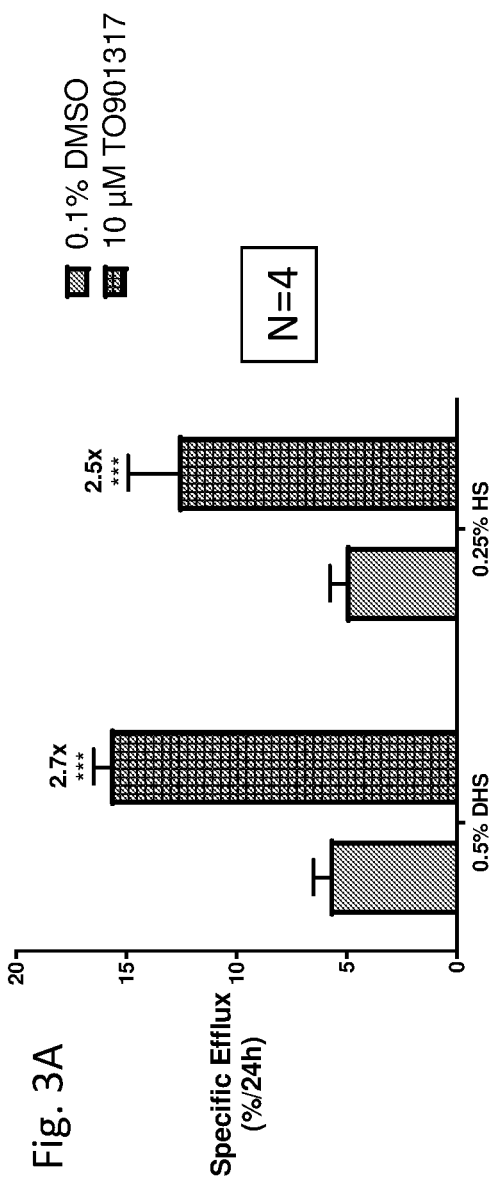
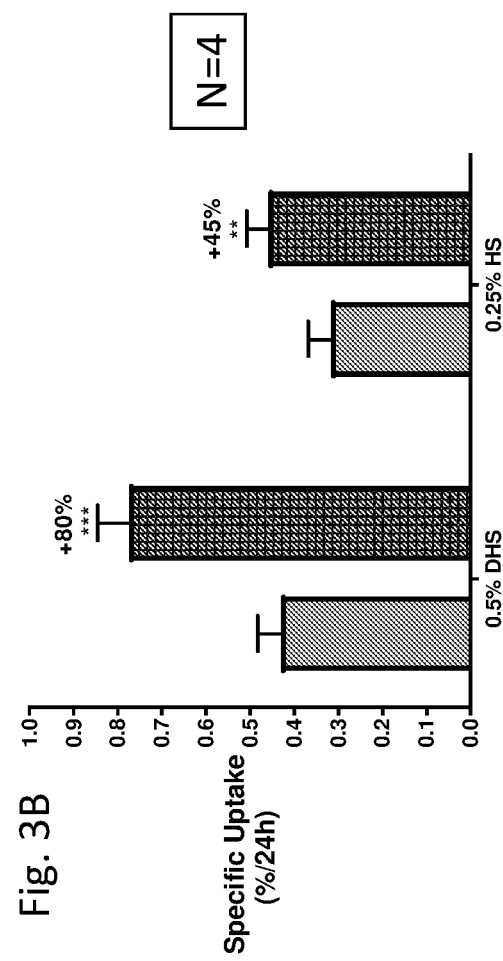
Fig. 3A
Fig. 3B

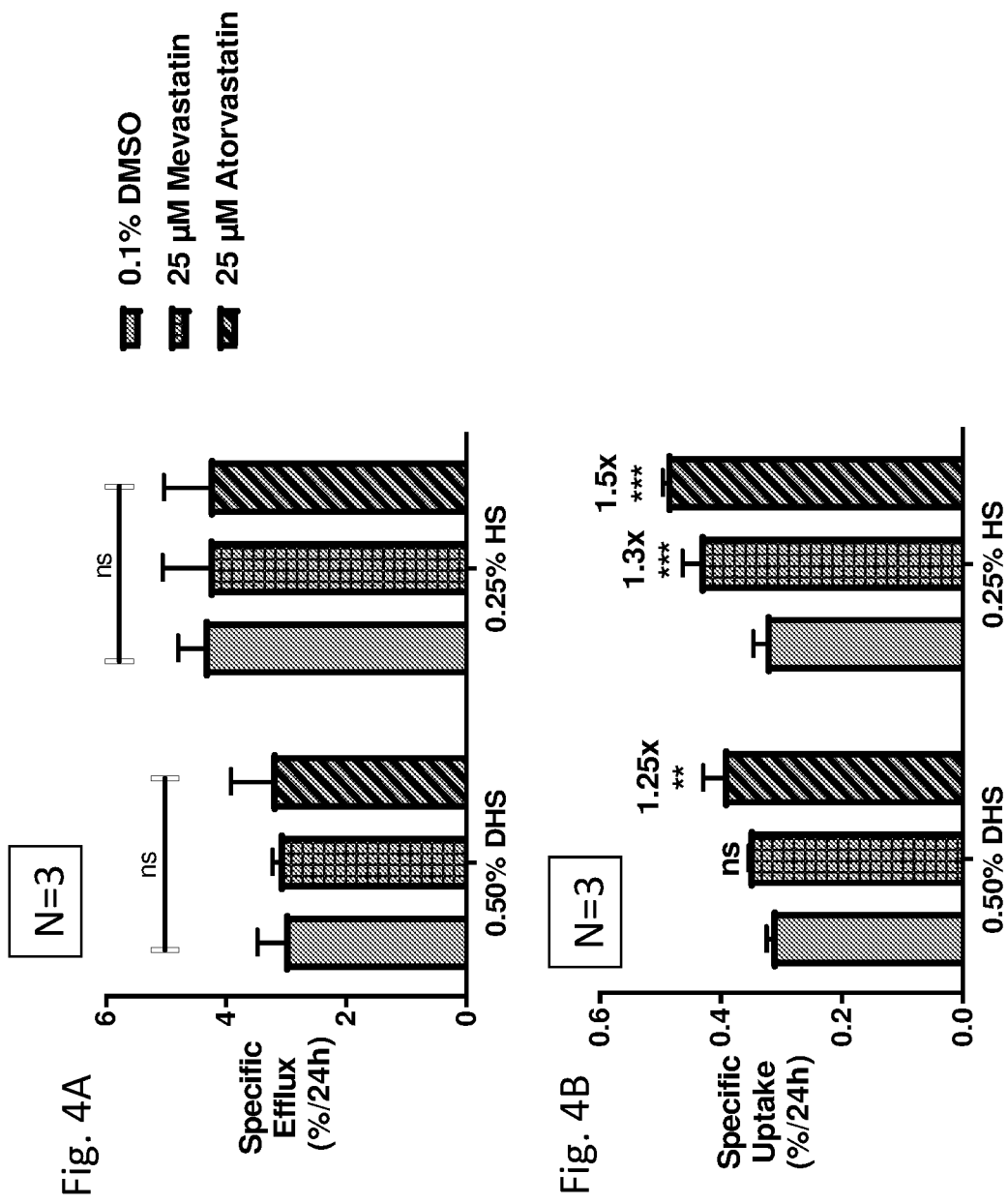

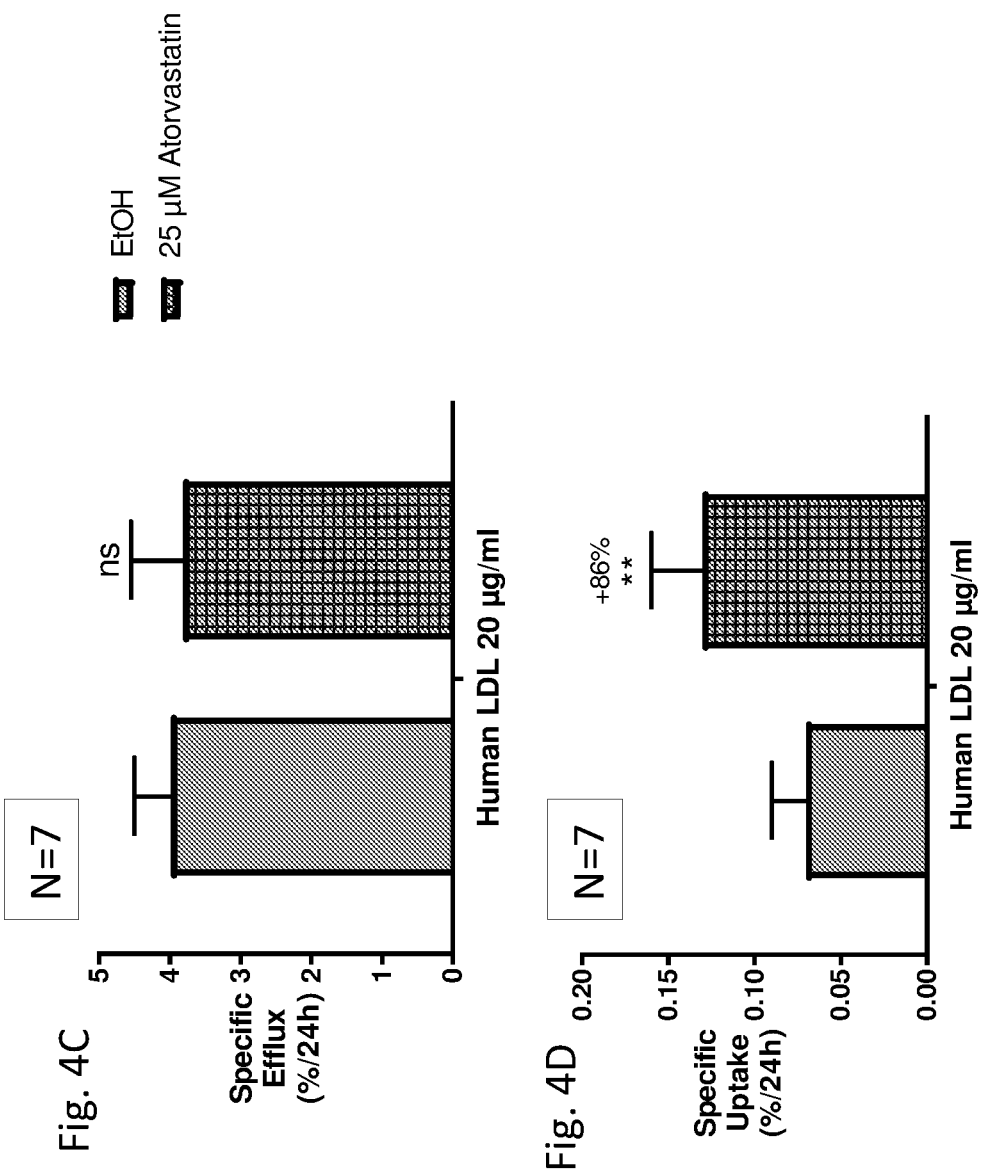

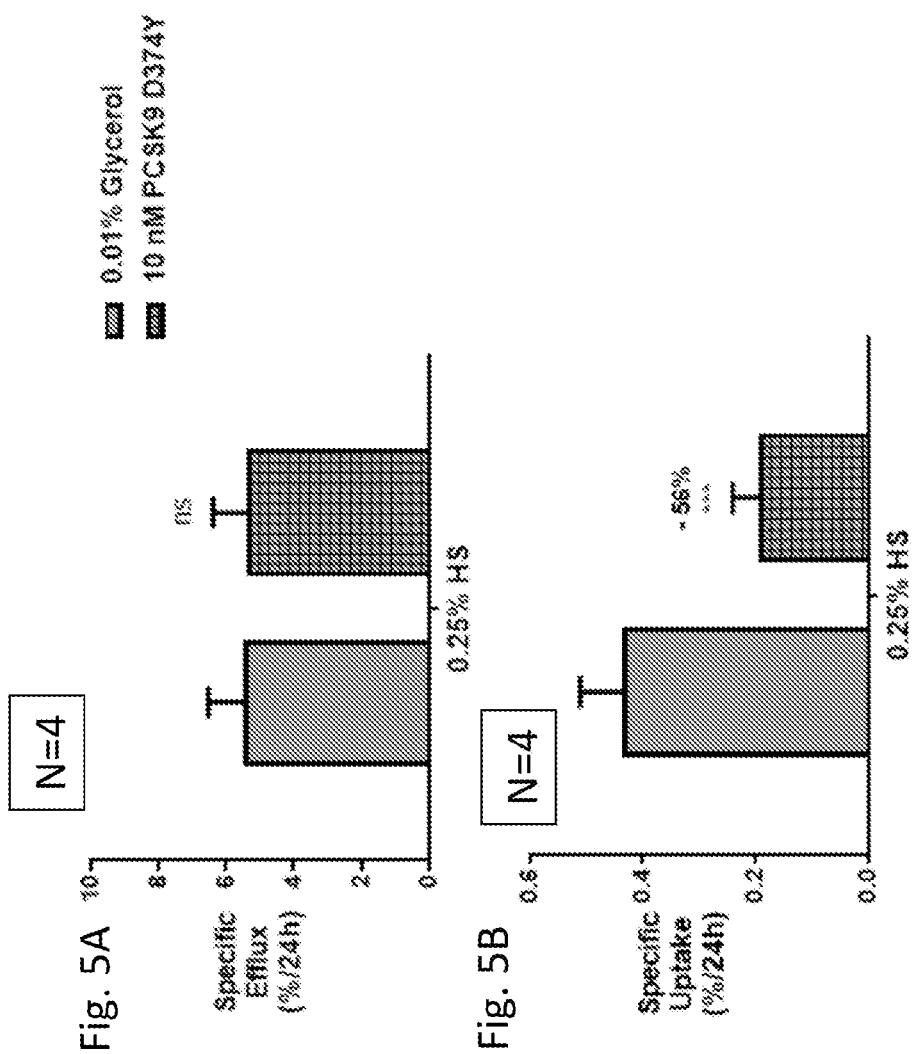

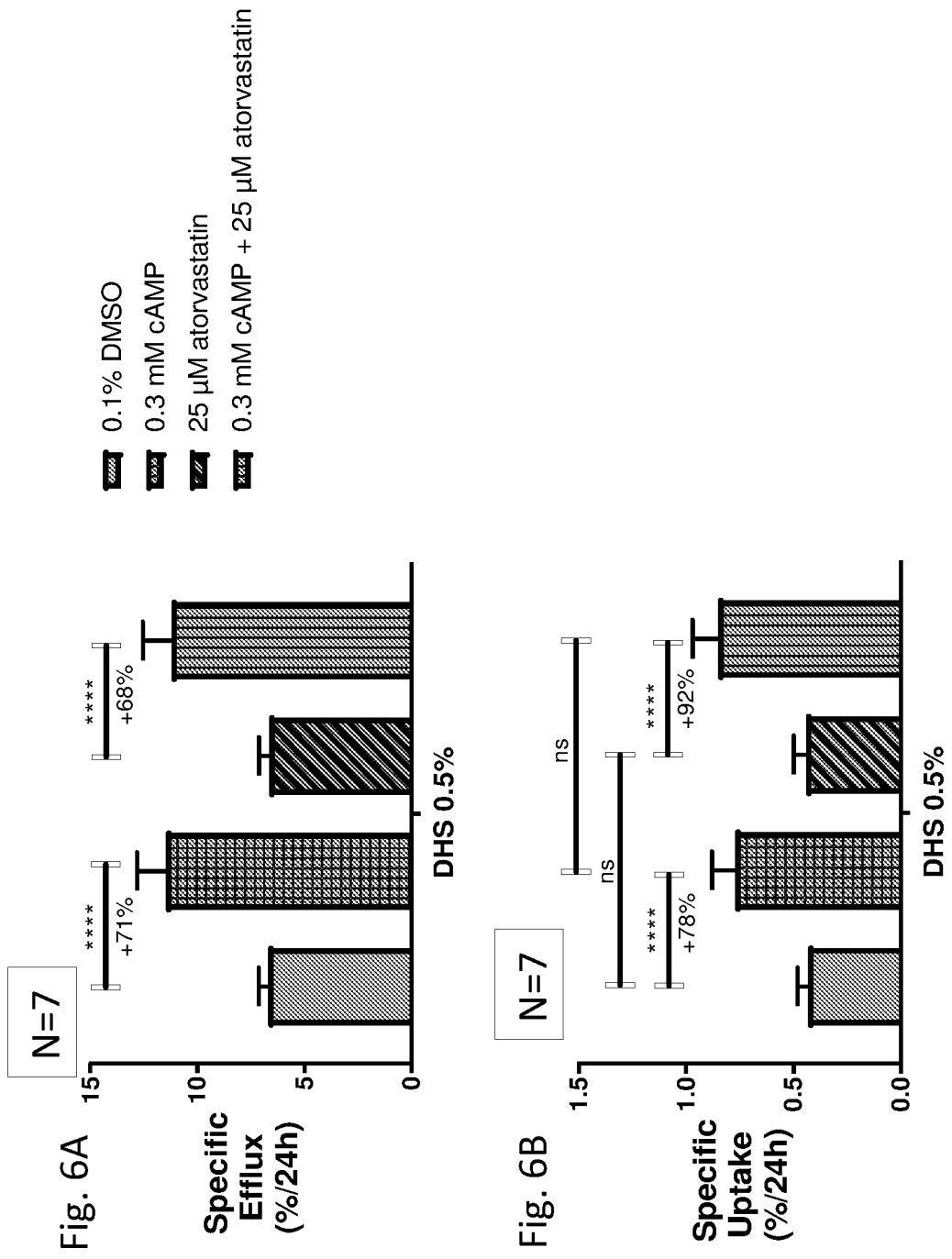

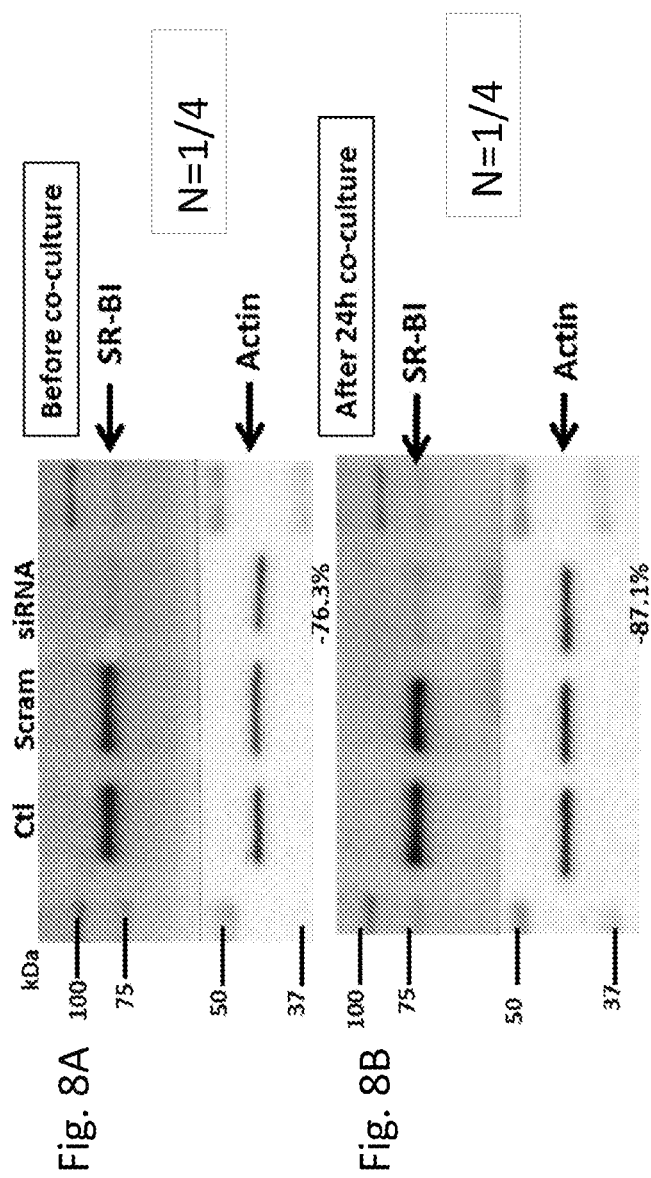

CO-CULTURE SYSTEM AND METHOD FOR IN VITRO ASSESSMENT OF REVERSE CHOLESTEROL TRANSPORT

FIELD OF THE INVENTION

The present invention belongs to the field of in vitro cellular assays and diagnostic testing.

BACKGROUND OF THE INVENTION

The high prevalence of cardiovascular disease (CVD) in North American countries has fostered the search for markers of CVD risk and incidence. Among those, cholesterol (Chol) efflux capacity of serum has emerged as a negative predictor of prevalent and incident CV diseases. However, Chol efflux is only the first step of reverse Chol transport (RCT), the process by which excess cholesterol from peripheral tissues is transported back to the hepatic parenchymal cells (hepatocytes) to be excreted in bile. In humans, RCT is comprised of unesterified Chol efflux to HDL from peripheral tissues, HDL maturation and partial esterification of its free cholesterol, partial transfer to apoB-containing particles (LDL and VLDL) via cholesteryl ester transfer protein, and Chol uptake from LDL by the hepatic LDL receptors and from HDL by the hepatic scavenger receptor class B, type I (SR-BI), followed by bile excretion. The so-called indirect reverse Chol transport by LDL and LDLR appears to be the major pathway in humans (Schwartz et al., 2004).

Current measurement of reverse Chol transport in vivo involves the use of metabolic tracer in animals (Tanigawa et al., 2007) or humans (Turner et al., 2012). This approach requires injection of radioactive- or stable-isotope tracers, repeated sampling of plasma and collection of feces and extraction of the tracer Chol over 72 hours. While liver uptake of the tracer could be ascertained by liver biopsy, it is not performed in humans. High variability between the actual injected dose in animals such as mice and inter-individual variability in mice and humans make this approach cumbersome for most laboratories. A further limitation is that it is not possible to test drugs that have not entered clinical development in humans, or to test heterologous samples from human subjects in mice.

Cell culture systems and assays are known for assessing Chol efflux mediated by human serum samples, e.g. U.S. Pat. No. 7,029,863 issued Apr. 4, 2006 to Rothblat and US Patent Application Publication US20110152112 published Jun. 23, 2011 an filed by Johansson. Such assays provide an incomplete assessment of Chol transport in that they can only be used to measure Chol efflux.

In view of the above, there is a need for an improved Chol transport assay. An object of the present invention is to provide such an assay.

SUMMARY OF THE INVENTION

The present invention provides a method for assessing simultaneously cellular Chol efflux and uptake in vitro, assessing Chol uptake via major hepatic pathways and their modulation by pharmacological treatments, biologics or genetic engineering.

The co-culture system of the invention is comprised of a co-culture of macrophage cells loaded with labeled Chol and hepatocyte cells. Macrophage cells for use in the system express transporter proteins that mediate Chol efflux from the macrophage into the culture medium, such as ABCA1, ABCG1 and SR-BI. In some embodiments, the macrophage cell is a mouse macrophage cell line, a human macrophage or monocyte-derived cell line or primary cultures of macrophages from any species, including stably or transiently genetically modified models (e.g. knockout, transgene over-expressing, genome-edited, transfected or infected with cDNA constructs). Hepatocyte cells for use in the invention express proteins that mediate Chol uptake from the culture medium into the hepatocyte cell, such as low-density lipoprotein receptor (LDLR), scavenger receptor class B, type 1 (SR-B1), CD36 and LDLR-related protein-1 (LRP-1). In some embodiments, the hepatocyte is a human hepatic cell line or a primary hepatocyte from human or other animal species or hepatocyte-like cells derived from stem cells such as induced pluripotent stem cells.

In one embodiment, the co-culture system is comprised of labeled-Chol-loaded macrophage cells cultured at the bottom of the wells of a cell culture plate and hepatocyte cells cultured on a porous membrane insert into each well containing the macrophage cells. In another embodiment, the system further comprises Chol acceptor molecules, which can be defined as molecular entities that bind cholesterol that has diffused from Chol donor cell membranes via passive or facilitated diffusion or active protein-mediated transport. Chol acceptors include, but are not limited to: complete serum, fractions of serum including apolipoprotein B-containing lipoproteins-depleted serum, purified lipoproteins such as HDL, reconstituted (recombinant) lipoprotein particles and purified proteins such as apolipoproteins, albumin or other cholesterol binding proteins.

The assay system of the invention mimics in vivo cholesterol transport and is comprised of macrophage and hepatocyte cells. The methods and systems of the invention can be used to evaluate the impact of Chol transport-modulating agent, e.g. a pharmacological agent, biological molecule or particular genetic modification of a cell, i.e. macrophage or hepatocyte cell, on cellular Chol efflux and uptake. Prior to incubation with hepatocyte cells, macrophage cells are loaded with Chol that is conjugated to or labeled with a detectable label e.g. a stable isotope, a radioactive isotope or a fluorescence label.

In some embodiments, the labeled macrophages are exposed to the Chol transport-modulating agent before incubation with hepatocytes. In other embodiments, the hepatocytes are exposed to the Chol transport-modulating agent before incubation with Chol-labeled macrophages. In other embodiments, macrophages and hepatocytes are co-incubated and simultaneously exposed to a Chol transport-modulating agent that acts on macrophages, hepatocytes or both cell types. Co-incubation involves cultivating macrophages and hepatocytes in separate layers bathed in a shared culture medium that allows Chol transport, but where mixing of the cells is prevented by the insert membrane supporting hepatocytes.

An assay that measures both Chol efflux and uptake simultaneously is advantageous because it captures an essential step in the reverse cholesterol transport process, the hepatic cholesterol uptake. Another advantage of such an assay is that it allows uptake of cholesterol in hepatic cells by pathways relevant to the human physiology via LDL (Schwartz et al., 2004) and HDL particles (Zanoni et al., 2016). Moreover, an assay that measures cholesterol efflux and uptake from serum lipoproteins incorporates important steps of the reverse cholesterol transport process such as free cholesterol esterification (US 2014/0322735) and cholesterol ester transfer via the cholesteryl ester transfer protein (Gautier et al., 2016).

In a broad aspect, the invention provides an in vitro assay system for measuring cholesterol (Chol) transport, comprising: Chol exporting cells; and hepatocytes; the Chol exporting cells and the hepatocytes being in a shared culture medium to allow Chol transport between the Chol exporting cells and the hepatocytes.

The invention may also provide an in vitro assay system wherein the Chol exporting cells and the hepatocytes are segregated from each other.

The invention may also provide an in vitro assay system wherein: the Chol exporting cells are contained and confined in a first cell culture vessel; the hepatocytes are contained and confined in a second cell culture vessel; and the culture medium permeates the first and second cell culture vessels with the first and second culture vessels in a fluid communication relationship with each other so that the culture medium can diffuse between the first and second cell culture vessels.

The invention may also provide an in vitro assay system wherein the first and second culture vessels are adjacent to each other and wherein a porous membrane is provided between the first and second culture vessels.

The invention may also provide an in vitro assay system wherein the second culture vessel is provided above the first culture vessel.

The invention may also provide an in vitro assay system wherein the hepatocytes are supported on the membrane.

The invention may also provide an in vitro assay system wherein the Chol exporting cells are immune cells.

The invention may also provide an in vitro assay system wherein the immune cells include cells selected from the group consisting of a mouse macrophage cell line, a human macrophage cell line, a monocyte-derived cell line, a primary culture of macrophages, a genetically modified macrophage cell line or a macrophage-like cell derived from induced plutipotent stem cells.

The invention may also provide an in vitro assay system wherein the Chol exporting cells include macrophages.

The invention may also provide an in vitro assay system wherein the macrophages express a transporter protein that mediates Chol efflux from the macrophages into the culture medium.

The invention may also provide an in vitro assay system wherein the transporter protein is ABCA1, ABCG1, ABCG4, ABCG7, an ABC transporter or SR-BI.

The invention may also provide an in vitro assay system wherein the macrophages include cells selected from the group consisting of murine cell lines J774A.1 (ATCC® TIB-67™), J774.2 (Sigma-Aldrich 85011428), LADMAC (ATCC® CRL-2420™), RAW 264.7 (ATCC® TIB-71™), RAW 309 (ATCC® TIB-69™), P388D1 (ATCC® CCL-46™), WEHI-265.1 (ATCC® TIB-204), and WEHI-274 (ATCC® CRL-1679), human cell lines THP-1 (ATCC® TIB-202™), JM1 (ATCC® CRL-10423™), KG-1 (ATCC® CCL-246™), U937 (ATCC® CRL-1593.2™), AML-193 (ATCC® CRL-9589™), MD (ATCC® CRL-9850), and SC (ATCC® CRL-9855), and macrophages derived from tissue resident macrophages, human induced pluripotent stem cells, monocyte cell lines, WEHi cells, THP-1 cells, primary monocytic cells, peripheral blood monocytic cells, CD14$^+$ cells.

The invention may also provide an in vitro assay system wherein the hepatocytes express proteins that mediate Chol uptake from the culture medium into the hepatocytes.

The invention may also provide an in vitro assay system wherein the proteins that mediate Chol uptake from the culture medium into the hepatocytes include at least one of a low-density lipoprotein receptor (LDLR), scavenger receptor class B, type 1 (SR-B1), CD36 and LDLR-related protein-1 (LRP-1).

The invention may also provide an in vitro assay system wherein the hepatocyte include cells selected from the group consisting of rodent cell lines AML-12 (ATCC® CRL-2254), H2.35 (ATCC® CRL-1995), FL83B (ATCC® CRL-2390), Fu5AH (Rothblat, 1974), and McA-RH777 (ATCC® CRL-1601), human cell lines HepG2 (ATCC® HB-8065), HepG2/2.2.1 (ATCC® CRL-11997™) Hep3B2.1-7 (ATCC® HB-8064), C3A (ATCC HB-8065 or (ATCC® CRL-10741), SK-HEP (ATCC® HTB-52), and HuH7 (Creative Bioarray, CSC-C9441L), hepatocytes derived from human induced pluripotent stem cells, and primary cultures of human or mouse hepatocytes.

The invention may also provide an in vitro assay system wherein the hepatocyte includes at least one of a human hepatic cell line or a primary hepatocyte.

The invention may also provide an in vitro assay system wherein the culture medium contains a Chol-acceptor.

The invention may also provide an in vitro assay system wherein the Chol-acceptor is albumin or a phospholipid vesicle.

The invention may also provide an in vitro assay system wherein the phospholipid vesicle is high-density lipoprotein or low-density lipoprotein.

The invention may also provide an in vitro assay system wherein at least one of the Chol exporting cells and culture medium includes labeled Chol.

The invention may also provide an in vitro assay system wherein the labeled Chol is labeled with a fluorescent or radioactive tracer.

The invention may also provide an in vitro assay system wherein the labeled Chol includes at least one of tritiated ($^3$H) Chol or $^{14}$C-labelled Chol.

The invention may also provide an in vitro assay system wherein the labeled Chol includes Chol covalently linked to a fluorophore.

The invention may also provide an in vitro assay system wherein the fluorophore is selected from the set consisting of boron-dipyrromethene (BODIPY) and nitrobenzoxadiazole (NBD).

The invention may also provide an in vitro assay system wherein the labeled Chol is a fluorescent cholesterol analog.

The invention may also provide an in vitro assay system wherein the fluorescent cholesterol analog is dehydroergosterol.

The invention may also provide an in vitro assay system wherein the culture medium includes a sample of human serum.

The invention may also provide an in vitro assay system wherein the human serum is depleted of apolipoprotein B.

The invention may also provide an in vitro assay system wherein the human serum is complete.

The invention may also provide an in vitro assay system wherein the culture medium includes at least one Chol acceptor.

The invention may also provide an in vitro assay system further comprising other Chol exporting cells and other hepatocytes in an other shared culture medium allowing Chol transport between the other Chol exporting cells and the other hepatocytes, the other culture medium being devoid of the at least one Chol acceptor.

The invention may also provide an in vitro assay system wherein the at least one Chol acceptor is selected from the group consisting of lipid-protein complexes, complexes of lipids with natural peptides, complexes of lipids with synthetic peptides and serum albumin.

The invention may also provide an in vitro assay system wherein the at least one Chol acceptor is selected from the group consisting of apoB-depleted serum, apoA-I, apoA-II, apoA-IV, apoA-V, apo(a), apoB, apoC-I, apoC-II, apoC-Ill, apoC-IV, apoD, apoE, apoJ, apoL1, apoM, apoO, apoO-like, CSL-111, CSL-112, CER-001, ETC-642, CER-522, ATI-5261, 5A, C-II-a and D4F.

The invention may also provide an in vitro assay system wherein the at least one Chol acceptor is in a concentration that avoids saturation of Chol efflux from the Chol exporting cells and that allows significantly greater Chol flux over Chol flux in absence of the Chol acceptor.

The invention may also provide an in vitro assay system wherein the Chol acceptor includes one of human complete serum at a concentration of about 0.25%, apoB-depleted human serum at a concentration of about 0.5% and high-density lipoprotein at a concentration of about 15 µg/mL.

The invention may also provide an in vitro assay system wherein the culture medium further comprises an upregulator or a downregulator of the activity of the Chol acceptor.

The invention may also provide an in vitro assay system wherein the upregulator or downregulator of the activity of the Chol acceptor is selected from the group consisting of LCAT, CETP, PLTP, LPL, HDL, EL, ANGPTL3, ANGPTL4, ANGPTL8, serum amyloid A, CRP, myeloperoxidase, paraoxonase, a blocking antibody, and a stimulatory antibody. Non-limiting examples of blocking antibodies include blocking antibodies developed against CETP or ANGPTL4 or apoC-Ill. A non-limiting example of a stimulatory antibody includes a stimulatory antibody for LCAT.

The invention may also provide an in vitro assay system wherein the culture medium contains a PCSK9 antagonist.

The invention may also provide an in vitro assay system wherein the PCSK9 antagonist is a PCSK9 blocking antibody.

The invention may also provide an in vitro assay system wherein the culture media contains a CETP inhibitor.

The invention may also provide an in vitro assay system wherein the CETP inhibitor is selected from torcetrapib, dalcetrapib, evacetrapib and anacetrapib.

The invention may also provide an in vitro assay system wherein at least some of the hepatocytes are transduced with a siRNA that reduces expression of hepatic HDL receptor SR-BI.

The invention may also provide an in vitro assay system wherein at least some of the hepatocytes overexpress hepatic HDL receptor SR-BI or an LDL receptor. Examples of manner of causing overexpression include vector transfection, virus infection or transduction of shRNA or ORF clone, silencing RNA and locked nucleic acid, among others.

The invention may also provide an in vitro assay system wherein the hepatocytes are pre-treated with a statin drug. For the purpose of this document, a statin drug is a HMG-CoA reductase inhibitor.

The invention may also provide an in vitro assay system wherein the statin drug is selected from atorvastatin and mevastatin.

The invention may also provide an in vitro assay system wherein the Chol exporting cells are pre-treated with an LXR agonist.

The invention may also provide an in vitro assay system wherein the LXR agonist is TO901317.

The invention may also provide an in vitro assay system wherein the culture medium includes a PCSK9 analog.

The invention may also provide an in vitro assay system wherein the culture medium includes human complete serum and the PCSK9 agonist is purified human PCSK9 gain-of-function D374Y mutant protein.

The invention may also provide an in vitro assay system wherein the Chol exporting cells are pre-treated with cyclic AMP (cAMP).

The invention may also provide an in vitro assay system wherein the cAMP is selected from the group consisting of 8-bromo-cAMP, chlorphenylthio-cAMP and dibutyryl-cAMP.

The invention may also provide an in vitro assay system wherein the hepatocytes are pre-treated with 5'-azacytidine.

In another broad aspect, the invention provides an in vitro method for assessing simultaneously cellular cholesterol (Choi) efflux and hepatic Chol uptake, the method comprising: (a) providing Chol exporting cells, the Chol exporting cells being loaded with labeled Chol; (b) providing hepatocytes; (c) culturing for a predetermined duration in a shared culture medium the Chol exporting cells and the hepatocytes; and (d) after the predetermined duration, quantifying Chol content in each of the culture medium, Chol-exporting cells and hepatocytes.

The invention may also provide a method wherein the culture medium and the hepatocytes contain essentially no labeled Chol before step (c) is performed; the quantity of Chol in the hepatocytes quantified at step (d) divided by the total of the quantities of Chol in the culture medium, Chol-exporting cells and hepatocytes quantified at step (d) is indicative of Chol uptake by the hepatocytes; and the sum of the quantities of Chol in the hepatocytes and in the culture medium quantified at step (d) divided by the total of the quantities of Chol in the culture medium, Chol-exporting cells and hepatocytes quantified at step (d) is indicative of Chol Efflux from the Chol-exporting cells.

The invention may also provide a method wherein the labeled Chol is labeled with at least one of a fluorescent tracer, a radioactive tracer, tritiated ($^3$H) Chol, $^{14}$C-labelled Chol, a covalently linked fluorophore, covalently linked boron-dipyrromethene (BODIPY) and covalently linked nitrobenzoxadiazole (NBD).

The invention may also provide a method wherein the labeled Chol is a fluorescent cholesterol analog.

The invention may also provide a method wherein the fluorescent cholesterol analog is dehydroergosterol.

The invention may also provide a method wherein steps (a) to (d) are performed for first and second culture media, wherein the first culture medium includes a Chol acceptor and the second culture medium is devoid of the Chol acceptor, differences in the quantification at step (d) of Chol content in each of the culture medium, Chol-exporting cells and hepatocytes for the cultures performed in the first and second culture media being indicative of the effect of the Chol acceptor on Chol efflux from the Chol-exporting cells, Chol uptake by the hepatocytes or both Chol efflux from the Chol-exporting cells and Chol uptake by the hepatocytes.

The invention may also provide a method wherein the Chol acceptor is albumin or a phospholipid vesicle.

The invention may also provide a method wherein the phospholipid vesicle is high-density lipoprotein or low-density lipoprotein.

The invention may also provide a method wherein the Chol acceptor is selected from the group consisting of lipid-protein complexes, complexes of lipids with natural peptides, complexes of lipids with synthetic peptides, an apo, an apo mimetic peptide, a phospholipid, serum albumin and mixtures thereof.

The invention may also provide a method wherein the Chol acceptor is selected from the group consisting of apoB-depleted serum, apoA-I, apoA-II, apoA-IV, apoA-V, apo(a), apoB, apoC-I, apoC-II, apoC-III, apoC-IV, apoD, apoE, apoJ, apoL1, apoM, apoO, apoO-like, CSL-111, CSL-112, CER-001, ETC-642, CER-522, ATI-5261, 5A, C-II-a and D4F.

The invention may also provide a method wherein at least one Chol acceptor is in a concentration that avoids saturation of Chol efflux from the other Chol-exporting cells and that allows significantly greater Chol flux between the other Chol-exporting cells and the hepatocytes over Chol flux in absence of the Chol acceptor.

The invention may also provide a method wherein the Chol acceptor includes one of human complete serum at a concentration of about 0.25%, apoB-depleted human serum at a concentration of about 0.5% and high-density lipoprotein at a concentration of approx. 15 µg protein/mL.

The invention may also provide a method wherein the culture medium further comprises an upregulator or a down-regulator of the activity of the Chol acceptor.

The invention may also provide a method wherein the Chol-exporting cells and the hepatocytes are segregated from each other during step (c).

The invention may also provide a method wherein, during step (c): the Chol-exporting cells are contained and confined in a first cell culture vessel; the hepatocytes are contained and confined in a second cell culture vessel; and the culture medium permeates the first and second cell culture vessels with the first and second culture vessels in a fluid communication relationship with each other so that the culture medium can diffuse between the first and second cell culture vessels.

The invention may also provide a method wherein the first and second culture vessels are adjacent to each other and wherein a porous membrane is provided between the first and second culture vessels.

The invention may also provide a method wherein the hepatocytes are supported on the membrane.

The invention may also provide a method wherein the Chol-exporting cells are immune cells.

The invention may also provide a method wherein the immune cells include cells selected from the group consisting of a mouse macrophage cell line, a human macrophage cell line, a monocyte-derived cell line, a primary culture of macrophages and a genetically modified immune macrophage cell line.

The invention may also provide a method wherein the Chol exporting cells include macrophages.

The invention may also provide a method wherein the macrophages express a transporter protein that mediates Chol efflux from the macrophages into the culture medium.

The invention may also provide a method wherein the transporter protein is ABCA1, ABCG1 or SR-BI.

The invention may also provide a method wherein the macrophages include cells selected from the group consisting of murine cell lines J774A.1 (ATCC® TIB-67™), J774.2 (Sigma-Aldrich 85011428), LADMAC (ATCC® CRL-2420™), RAW 264.7 (ATCC® TIB-71™), RAW 309 (ATCC® TIB-69™), P388D1 (ATCC® CCL-46™), WEHI-265.1 (ATCC® TIB-204), and WEHI-274 (ATCC® CRL-1679), human cell lines THP-1 (ATCC® TIB-202™), JM1 (ATCC® CRL-10423™), KG-1 (ATCC® CCL-246™), U937 (ATCC® CRL-1593.2™), AML-193 (ATCC® CRL-9589™), MD (ATCC® CRL-9850), and SC (ATCC® CRL-9855), and macrophages derived from tissue resident macrophages, human induced pluripotent stem cells, monocyte cell lines, WEHi cells, THP-1 cells, primary monocytic cells, peripheral blood monocytic cells, $CD14^+$ cells.

The invention may also provide a method wherein the hepatocytes express proteins that mediate Chol uptake from the culture medium into the hepatocytes.

The invention may also provide a method wherein the proteins that mediate Chol uptake from the culture medium into the hepatocytes include at least one of a low-density lipoprotein receptor (LDLR), scavenger receptor class B, type 1 (SR-B1), CD36 and LDLR-related protein-1 (LRP-1).

The invention may also provide a method wherein the hepatocyte include cells selected from the group consisting of rodent cell lines AML-12 (ATCC® CRL-2254), H2.35 (ATCC® CRL-1995), FL83B (ATCC® CRL-2390), Fu5AH (Rothblat, 1974), and McA-RH777 (ATCC® CRL-1601), human cell lines HepG2 (ATCC® HB-8065), HepG2/2.2.1 (ATCC® CRL-11997™) Hep3B2.1-7 (ATCC® HB-8064), C3A (ATCC HB-8065 or (ATCC® CRL-10741), SK-HEP (ATCC® HTB-52), and HuH7 (Creative Bioarray, CSC-C9441L), hepatocytes derived from human induced pluripotent stem cells, and primary cultures of human or mouse hepatocytes.

The invention may also provide a method wherein the hepatocyte includes at least one of a human hepatic cell line and a primary hepatocyte.

The invention may also provide a method wherein the culture medium includes a sample of complete human serum.

The invention may also provide a method wherein the culture medium includes human serum depleted of apolipoprotein B.

The invention may also provide a method wherein the culture medium contains a PCSK9 antagonist.

The invention may also provide a method wherein the PCSK9 antagonist is a PCSK9 blocking antibody.

The invention may also provide a method wherein the culture media contains a CETP inhibitor.

The invention may also provide a method wherein the CETP inhibitor is selected from torcetrapib, dalcetrapib and anacetrapib.

The invention may also provide a method wherein at least some of the hepatocytes are transduced with a siRNA that reduces expression of hepatic HDL receptor SR-BI.

The invention may also provide a method wherein at least some of the hepatocytes overexpress hepatic HDL receptor SR-BI or an LDL receptor.

The invention may also provide a method wherein step (b) includes exposing the hepatocytes to a statin drug.

The invention may also provide a method wherein the statin drug is selected from atorvastatin and mevastatin.

The invention may also provide a method wherein step (a) includes exposing the Chol-exporting cells with to LXR agonist.

The invention may also provide a method wherein the LXR agonist is TO901317.

The invention may also provide a method wherein the culture medium includes a PCSK9 agonist.

The invention may also provide a method wherein the culture medium includes human complete serum and the PCSK9 agonist is purified human PCSK9 gain-of-function D374Y mutant protein.

The invention may also provide a method wherein step (a) includes exposing the Chol exporting cells to cyclic AMP.

The invention may also provide a method wherein the cAMP is selected from the group consisting of 8-bromo-cAMP, CPT-cAMP and dibutyryl-cAMP.

The invention may also provide a method wherein step (b) includes exposing the hepatocytes to 5'-azacytidine.

In yet another broad aspect, the invention provides an in vitro assay system for measuring cholesterol (Chol) transport, comprising: cells expressing a Chol transporter; and Chol accepting cells; the cells expressing a Chol transporter and the Chol accepting cells being in a shared culture medium to allow Chol transport between the cells expressing a Chol transporter and the Chol-accepting cells.

For example, and non-limitingly, the cells expressing the Chol transporter may be Chol-exporting cells, such as macrophages and other related immune cells, or other cells that express a chol transporter such as HEK or COS or CHO cells transfected with ABCA1. Other examples of Chol-exporting cells include cells with capacity to form a foam, such as smooth muscle cell-derived foam cell. For example, and non-limitingly, the Chol-accepting cells are hepatocytes or other Chol-accepting cells, such as some intestinal cells, for example enterocytes.

In yet another broad aspect, the invention provides an in vitro method for assessing simultaneously cellular cholesterol (Chol) efflux and Chol uptake, the method comprising: (a) providing cells expressing a Chol transporter, the cells expressing a Chol transporter being loaded with labeled Chol; (b) providing Chol-accepting cells; (c) culturing for a predetermined duration in a shared culture medium the cells expressing a Chol transporter and the Chol-accepting cells; and (d) after the predetermined duration, quantifying Chol content in each of the culture medium, cells expressing a Chol transporter and Chol-accepting cells.

The term "providing" means that the cells are somehow brought where they can be used. This may include buying or otherwise obtaining cell samples, for example by isolating such cells from a living organism, as well as making a culture of cells to increase their number.

Labeled Chol is cholesterol that has been modified to allow quantification of its amount in a sample, for example and non-limitingly through scintillation or fluorescence. Quantification can be made with a whole component of the proposed assay, for example all the hepatocytes contained in the first compartment, or an aliquot thereof. Quantification can relate to the total quantity of Chol, the concentration of Chol or the fraction of all the Chol contained in part of the assay, among other possibilities. If the total amount of Chol introduced in the assay is known, in some embodiments, Chol can be quantified in each of the Chol-exporting cells, hepatocytes and culture medium by only directly measuring Chol in two of these possible Chol locations and deducing the Chol in the remaining possible location by simply subtracting the two measured Chol quantities from the known total Chol content of the assay. However, in this same situation, quantifying Chol in the Chol-exporting cells, hepatocytes and culture medium can also be performed. Cells are loaded with labeled Chol when at least part of the Chol present in the cells is labeled. Typically, there remains some unlabeled Chol in the Chol-loaded cell. In some embodiments, macrophages or hepatocytes are genetically modified before the co-culture phase to induce or reduce expression of a target gene at the mRNA and protein level.

The present invention claims priority from U.S. provisional patent application No. 62/343,388 filed on May 31, 2016, the contents of which is hereby incorporated by reference in its entirety.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIGS. 2A to 2D illustrate the dose-response of Chol flux with human HDL, LDL and apoA-I in co-culture. Increasing concentrations of human HDL or LDL (0-300 µg/ml) or apoA-I (0-100 µg/ml) as Chol acceptors were incubated for 24 hours in the co-culture system. Specific Chol Efflux and Uptake were determined by beta counting of aliquots from co-culture medium, J774 macrophage lysates and insert membrane with HepG2 cells. Specific Chol Efflux and Uptake were measured simultaneously with HDL or LDL (FIGS. 2A and 2B) or apoA-I (FIGS. 2C and 2D) in the co-culture system and they show saturation as a function of dose over the 24-hour co-culture. Specific Chol Efflux (%)=(% Efflux in presence of acceptor−% Efflux without acceptor [basal medium]), where % Efflux=(medium counts+hepatic cell counts)/(total counts in co-culture). Specific Uptake (%)=(% Uptake in presence of acceptor−% Uptake without acceptor [basal medium]), where % Uptake=(hepatic cell counts)/(total counts in co-culture). ApoA-I: human apolipoprotein A-I; HDL: total human high-density lipoproteins; LDL: human low-density lipoproteins.

FIGS. 3A and 3B illustrate the effect of an LXR agonist on Chol flux in co-culture. Before the co-culture assay, J774 macrophages were treated overnight with 10 µM TO901317, an LXR agonist that upregulates the ABCA1 and ABCG1 transporters for cholesterol efflux towards HDL. Co-culture was performed for 24 hours in presence of representative doses of human serum (complete and apoB-depleted). Chol Efflux and Uptake were determined by beta counting of aliquots from co-culture medium, J774 macrophage lysates and insert membrane HepG2 cells. Upregulation of cholesterol efflux transporters increased Specific Chol Efflux in presence of human serum (complete or apoB-depleted) (FIG. 3A) and resulted in a simultaneous increase of Specific Chol Uptake (FIG. 3B) in presence of human serum (complete or apoB-depleted). Specific Efflux (%)=(% Efflux in presence of acceptor−% Efflux without acceptor [basal medium]), where % Efflux=(medium counts+hepatic cell counts)/(total counts in co-culture). Specific Uptake (%)=(% Uptake in presence of acceptor−% Uptake without acceptor [basal medium]), where % Uptake=(hepatic cell counts)/(total counts in co-culture). HS: human serum; DHS: apoB-depleted human serum.

FIGS. 4A to 4D illustrate the effect of HMG-CoA reductase inhibitors (statins) on Chol flux in co-culture. Before the co-culture assay, HepG2 cells were treated overnight with 25 µM atorvastatin or 25 µM mevastatin, two 3-hydroxy-3-methylglutaryl-CoA reductase inhibitors that upregulate LDL receptor expression in hepatocytes. Co-culture was performed for 24 hours in presence of representative doses of human serum (complete and apoB-depleted) or human LDL. Specific Chol Efflux and Specific Chol Uptake were determined by beta counting of aliquots from co-culture medium, J774 macrophage lysates and insert membrane HepG2 cells. Both statins did not change Specific Chol Efflux (FIG. 4A), but significantly increased Specific Chol Uptake (FIG. 4B) with complete human serum containing LDL and VLDL. Statins had a reduced effect on Specific Chol Uptake with apoB-depleted serum, which contains HDL (FIG. 4B). Atorvastatin increased Specific Chol Uptake from human LDL (FIG. 4D) and did not modulate Specific Chol Efflux (FIG. 4C) as expected. Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). HS: human serum; DHS: apoB-depleted human serum.

FIGS. 5A and 5B illustrate the effect of a PCSK9 gain-of-function mutant on Chol flux in co-culture. Purified human PCSK9 protein with the D374Y gain-of-function mutation was added at 10 nM in culture medium and incubated during co-culture for 24 hours in presence of a representative dose of complete human serum (containing VLDL and LDL). Specific Chol Efflux and Uptake were determined by beta counting of aliquots from co-culture medium, J774 macrophage lysates and insert membrane HepG2 cells. Addition of purified PCSK9 mutant to the co-culture medium did not influence Specific Efflux in presence of complete serum containing LDL (FIG. 5A), but markedly reduced Specific Uptake from complete serum (FIG. 5B) most likely through the LDL receptor pathway. Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). HS: human serum.

FIGS. 6A to 6D illustrate the effect of J774 macrophage treatment with cyclic AMP (cAMP) and/or HepG2 cells with atorvastatin on Chol flux in co-culture. Before the co-culture assay, J774 macrophages were treated overnight with 300 µM 8-bromo-cAMP to induce cholesterol transporters of the ABC family, and/or HepG2 cells were treated overnight with 25 µM atorvastatin, a 3-hydroxy-3-methylglutaryl-CoA reductase inhibitor that upregulates LDL receptor expression in hepatocytes. Co-culture was performed for 24 hours in presence of representative doses of human serum (complete and apoB-depleted). Specific Chol Efflux and Specific Chol Uptake were determined by beta counting of aliquots from co-culture medium, J774 macrophage lysates and insert membrane HepG2 cells. cAMP increased Specific Chol Efflux in presence of both complete human serum and apoB-depleted serum (FIG. 6A, 6C). Treating HepG2 cells with atorvastatin did not modulate Specific Chol Efflux in presence or absence of cAMP treatment of macrophage, as expected (FIG. 6A, 6C). However, treating HepG2 cells with atorvastatin increased Specific Chol Uptake from complete human serum (containing VLDL and LDL) (FIG. 6B), but not from apoB-depleted serum (FIG. 6D). Treating HepG2 cells with atorvastatin had an additive effect to macrophage cAMP treatment on Specific Chol Uptake from complete serum (FIG. 6B), but not from apoB-depleted serum (FIG. 6D). Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). HS: human serum; DHS: apoB-depleted human serum.

FIGS. 8A to 8D illustrate the effect of silencing RNA against human SR-BI in HepG2 cells on Chol flux in co-culture. 48 hours before the co-culture assay, HepG2 cells were transfected twice at 24-hour interval with 6 pmol of siRNA mix against human SR-BI (Thermo-Fisher) or a scrambled non-silencing RNA and incubated in co-culture for 24 hours in presence of a representative dose of human serum (complete and apoB-depleted) or human HDL. Using western blot quantification and beta-actin normalization, SR-BI protein knockdown was 76% before the co-culture (FIG. 8A) and 87% at the end (FIG. 8B) in one representative experiment of n=4. Specific Chol Efflux and Uptake were determined by beta counting of aliquots from co-culture medium, J774 macrophage lysates and insert membrane HepG2 cells. Knockdown of hepatic cell SR-BI, a receptor involved in selective cholesterol uptake from HDL, had no effect on Specific Efflux (FIG. 8C), but reduced Specific Uptake (FIG. 8D) in presence of human HDL or HDL-enriched serum (apoB-depleted). Specific Uptake from complete serum containing LDL was not affected (FIG. 8D). Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). HS: human serum; DHS: apoB-depleted human serum; HDL: human high-density lipoproteins.

DETAILED DESCRIPTION

Figure 1A:
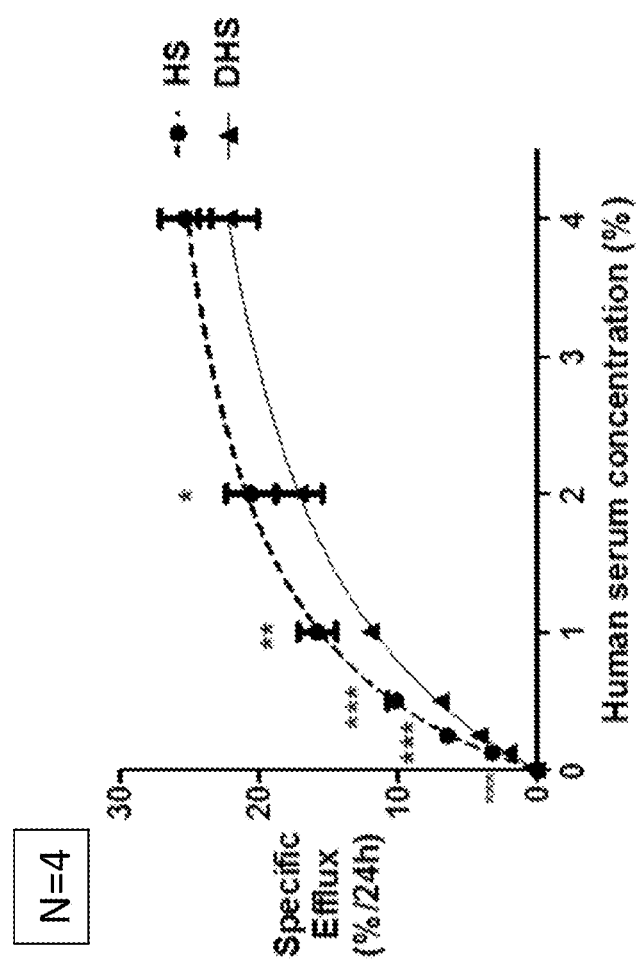
FIGS. 1A and 1B illustrate the dose-response of Chol flux with human serum in co-culture. Increasing concentrations of pooled normal human serum containing Chol acceptors (either complete serum or serum depleted of apoB-containing lipoproteins VLDL and LDL by precipitation (Asztalos et al. 2005)) were incubated for 24 hours in the co-culture system. The co-culture system consisting of: (1) a J774 macrophage culture containing intracellular isotope-labeled-Chol and (2) HepG2 hepatocytes cultured on a membrane insert, were incubated together in culture media. Following incubation with Chol acceptors, Specific Chol Efflux (FIG. 1A) and Uptake (FIG. 1B) were determined by beta counting of aliquots from: (1) co-culture medium, (2) J774 macrophage lysate and (3) HepG2 cells, i.e. measured in the 3 compartments of the co-culture system. Specific Chol Efflux and Specific Chol Uptake were measured simultaneously with complete serum and apoB-depleted serum in the co-culture system and both show saturation as a function of Chol acceptor dose over the 24-hour co-culture. Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). HS: human serum; DHS: apoB-depleted human serum.

Unless otherwise indicated or defined, all terms used have their usual meaning in the art to which the present invention relates. Reference is for example made to the standard handbooks, such as Sambrook et al., "Molecular Cloning: A Laboratory Manual", 4$^{th}$ Ed. Cold Spring Harbor Laboratory Press (2012); F. Ausubel et al., eds., "Current protocols in molecular biology", Wiley Interscience, (2012); Lewin, "Genes C", Jones & Bartlett Learning (2011); and Janeway et al., "Immunobiology" (7$^{th}$ Ed.), Garland Science (2008). The terminology used herein is to describe particular embodiments only and not intended to be limiting.

Throughout this disclosure, various publications, patents and published patent specifications are referenced by publication number or an identifying citation. The disclosures of these publications, patents and published patent application specifications are hereby incorporated by reference in their entirety into the present disclosure to more fully describe the state of the art to which this invention pertains.

Macrophage Cell Lines for Use in the Invention

Macrophage cell lines for use in the invention include murine cells (e.g. J774A.1 (ATCC® TIB-67™), J774.2 (Sigma-Aldrich 85011428), LADMAC (ATCC® CRL-2420™), RAW 264.7 (ATCC® TIB-71™), RAW 309 (ATCC® TIB-69™), P388D1 (ATCC® CCL-46™), WEHI-265.1 (ATCC® TIB-204), WEHI-274 (ATCC® CRL-1679) and human cells (e.g. THP-1 (ATCC® TIB-202™), JM1 (ATCC® CRL-10423™), KG-1 (ATCC® CCL-246™), U937 (ATCC® CRL-1593.2™), AML-193 (ATCC® CRL-9589™), MD (ATCC® CRL-9850), SC (ATCC® CRL-9855). Other types of macrophage cell lines for use in the invention include macrophages derived from: tissue resident macrophages (peritoneal cavity, bone marrow), human induced pluripotent stem cells, monocyte cell lines e.g. WEHi cells or THP-1 cells, or primary monocytic cells (peripheral blood monocytic cells, CD14±) of mouse or human origin, among other possibilities.

Hepatocyte Cell Lines for Use in the Invention

Hepatocyte cell lines for use in the invention include rodent cell lines: AML-12 (ATCC® CRL-2254), H2.35 (ATCC® CRL-1995), FL83B (ATCC® CRL-2390), Fu5AH (Rothblat, 1974), McA-RH777 (ATCC® CRL-1601) and human: HepG2 (ATCC® HB-8065), HepG2/2.2.1 (ATCC® CRL-11997™) Hep3B2.1-7 (ATCC® HB-8064), C3A (ATCC HB-8065 or (ATCC® CRL-10741), SK-HEP (ATCC® HTB-52), HuH7 (Creative Bioarray, CSC-C9441L) hepatic cell lines, hepatocytes derived from human induced pluripotent stem cells, and primary cultures of human or mouse hepatocytes, among other possibilities.

Cholesterol Labeling and Detection Methods

The assays of the invention use labeled Chol. Chol can be labeled in a variety of ways known in the art and detected in the co-culture media, macrophage or hepatocyte homogenate or cell lysate. In one embodiment, cells are labeled with tritiated ($^3$H) cholesterol or $^{14}$C-labelled cholesterol and the radioactive tracer is detected with beta-counting in the culture medium or cell homogenates in presence of scintillation cocktail. Labeled cells are termed "donor cells" as they can donate Chol to acceptors in the culture medium via multiple pathways: passive diffusion, ABCA1- and ABCG1-, SR-BI-mediated transport (Phillips, 2014).

In a further embodiment, donor cells are labeled with a fluorescent Chol derivative, where cholesterol is covalently linked to a fluorophore such as, among others, boron-dipyrromethene (BODIPY) (e.g. Avanti #810255) or nitrobenzoxadiazole (NBD) (e.g. Avanti #810250) or with a fluorescent cholesterol analog such as dehydroergosterol (Avanti #810253). Chol is detected by spectrofluorometry (plate reader) directly in the medium or in cell homogenates.

Macrophage and Hepatocyte Cell Culture Methods

Macrophages and hepatocytes are cultured separately in culture plates (macrophages) and Transwell™ inserts (hepatocytes) and subsequently co-cultured or co-incubated with a biological sample or media containing Chol-acceptor molecules. Cells can be treated independently with a drug, compound or modulator of interest prior to combining the 2 cell types, e.g. in a macrophage- or hepatocyte-only culture or even the 2 cell types before they are co-cultured. Alternatively, a drug, compound or modulator of interest can be added to the co-culture containing both cell types.

In one embodiment, the assay involves the steps of: culturing macrophages (J774) in Dulbecco's Minimal Essential Medium (DMEM, high glucose), (4.5 g/L) culturing hepatocytes in Eagle's Essential Minimal Medium (EMEM, low glucose), (1 g/L) seeding macrophages in 12-well cell culture plates. In a separate plate, hepatocytes are seeded in Transwell-Clear inserts (Corning #3462) with a 1.12 cm$^2$ PET membrane and a 3.0 µm pore size. Inserts with hepatocytes are transferred to the macrophage containing 12-well plate to initiate co-culture in DMEM high glucose, without phenol red, as basal medium.

Cholesterol Acceptor Molecules

Chol acceptors can be added to co-culture medium as serum or fractions of serum. Chol acceptors include naturally occurring or synthetic lipid-protein complexes such as apoB-depleted serum, isolated lipoproteins or apolipoproteins (including apoA-I (GeneID 335), apoA-II (GeneID 336), apoA-IV (GeneID 337), apoA-V (GeneID 116519), apo(a) (GeneID 4018), apoB (GeneID 338), apoC-I (GeneID 341), apoC-II (GeneID 344), apoC-III (GeneID 345), apoC-IV (GeneID 346), apoD (GeneID 347), apoE (GeneID 348), apoJ (GeneID 1191), apoL1 (GeneID 8542), apoM (GeneID 55937), apoO (GeneID 79135) and apoO-like (Gene ID 139322). Synthetic acceptors can be complexes of lipids with natural peptides (including CSL-111 (Tardif et al., 2007), CSL-112 (Tricoci et al., 2015), CER-001 (Tardy et al., 2014)) or with synthetic peptides (including apolipoprotein mimetic peptides such as ETC-642 (Di Bartolo et al., 2011), CER-522 (Merlet et al., 2016), ATI-5261 (Hafiane et al., 2014), 5A (Amar et al., 2010), C-II-a ((Amar et al., 2015) or D4F (Qin et al., 2012)). Serum albumin is also a significant cholesterol acceptor (Li et al., 2013). Basal culture medium is used to estimate Chol flux in the absence of test acceptors (background flux).

Chol acceptor is added at a concentration that avoids saturation of macrophage efflux and hepatocyte uptake allowing modulation of fluxes from both cell types to be properly quantified. Chol acceptors are also added at a concentration allowing significant Chol flux over the background given by basal medium.

Chol tracer distributes in both LDL and HDL particles when human serum is used as an acceptor, the proportion in LDL and HDL depending on the serum dose.

Compartments of the System Used to Measure Cholesterol Fluxes

The co-culture system is comprised of three compartments in which cholesterol can be traced. Firstly, macrophage cells (e.g. J774), secondly, the co-culture medium (with or without acceptors) and, thirdly, the hepatocyte cells (e.g. HepG2). At the end of the co-culture assay, radioactive counts are measured by beta counting in an aliquot of culture medium and in the total macrophage or hepatic compartment. The hepatic compartment is taken as counts on the insert membrane supporting hepatocyte cells.

Calculation of Measures of Efflux or Uptake

Total Chol Efflux is the sum of co-culture medium counts plus hepatic counts, while Total Chol Uptake is defined as hepatic counts only. Both Chol Efflux and Chol Uptake are expressed as % of total counts in the system. Background values, corresponding to basal co-culture medium (without acceptors), can be subtracted from the corresponding values in presence of acceptors to obtain Specific Chol Efflux (%) and Specific Chol Uptake (%) values.

Physical Format of the Assay.

Figure 10:
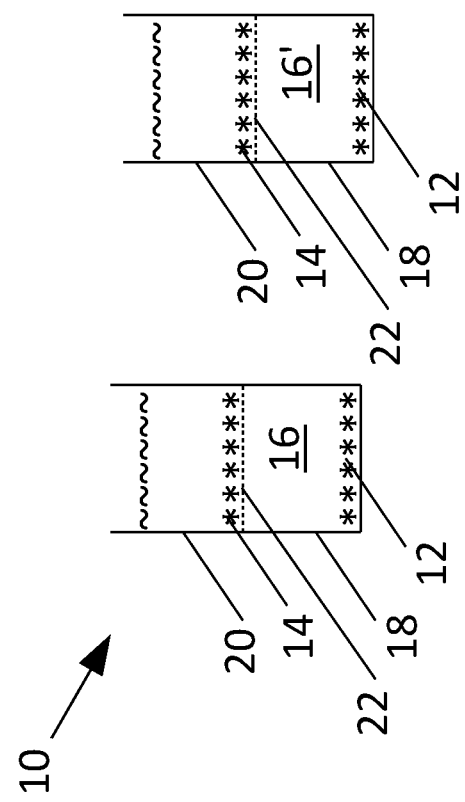

Generally speaking, and with reference to FIG. 10, the present invention relates in some embodiments to an in vitro assay system 10 for measuring cholesterol (Choi) transport, comprising Chol-exporting cells 12 and hepatocytes 14. The Chol-exporting cells 12 and the hepatocytes 14 are in a shared culture medium 16 to allow Chol transport between the Chol-exporting cells 12 and the hepatocytes 14.

The Chol-exporting cells 12 and the hepatocytes 14 could be mixed together in the culture medium 16 in some embodiments. However, some measurements related to the assay would require separation of the Chol-exporting cells 12 and hepatocytes 14 from each other before being taken. In situations in which this is easily performed, for example when one of the Chol-exporting cells 12 and the hepatocytes 14 has been marked or labeled in a manner allowing such separation easily, such a mixture of the Chol-exporting cells 12 and the hepatocytes 14 can be used.

However, it was found advantageous in some embodiments to segregate the Chol-exporting cells 12 and the hepatocytes 14 from each other so that each of the Chol-exporting cells 12 and the hepatocytes 14 can be manipulated and analyzed separately from each other. In a specific embodiment of the invention, as shown in FIG. 10, the Chol-exporting cells 12 are contained and confined in a first cell culture vessel 18 and the hepatocytes 14 are contained and confined in a second cell culture vessel 20. The culture medium 16 permeates the first and second cell culture vessels 18 and 20 with the first and second culture vessels 18 and 20 in a fluid communication relationship with each other so that the culture medium 16 can diffuse between the first and second cell culture vessels 18 and 20.

In a very specific embodiment of the invention, the first and second culture vessels 18 and 20 are adjacent to each other and a porous membrane 22 is provided between the first and second culture vessels 18 and 20. For example, the second culture vessel 20 is provided above the first culture vessel 18, but the reverse is also within the scope of the present invention. In some embodiments, the hepatocytes 14 are supported on the membrane 22.

It should be noted that other manners of segregating the Chol exporting cells 12 and hepatocytes 14 are also possible. For example, and non-limitingly, the hepatocytes could be in a pouch or other porous enclosure immersed in a compartment in which the Chol exporting cells 12 are provided. In other embodiments, one or both the Chol-exporting cells 12 and hepatocytes 14 can be supported on polymer beads or encapsulated in a porous substrate so that such cells can easily be separated from the remainder of the essay through mechanical means.

In some embodiments, the proposed assay includes many culture system including the Chol-exporting cells 12 and hepatocytes 14 segregated from each other, the many culture systems differing for example in the composition of the culture medium 16, 16'. For example, one of the culture medium 16 includes a Chol acceptor, and the other culture medium 16' is deprived of the Chol acceptor, as detailed hereinbelow.

Definitions

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; and so forth.

Unless otherwise indicated all methods steps and techniques mentioned herein can be performed in a manner known per se, as will be clear to the skilled person.

"Anti-atherosclerotic agent" means a peptide or a composition or formulation thereof that has an anti-atherosclerotic effect in vivo.

The term "antibody" is used herein in the broadest sense and specifically covers intact monoclonal antibodies, polyclonal antibodies, multi-specific antibodies (e.g. bi-specific antibodies) formed from at least two intact antibodies, and antibody fragments. "Antibody fragments" comprise only a portion of an intact antibody, generally including an antigen binding site of the intact antibody and thus retaining the ability to bind antigen. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed usually against a single antigen.

A "control" is an alternative subject or sample used in an experiment for comparison purpose. A control can be "positive" or "negative". For example, where the purpose of the experiment is to determine a correlation of an altered expression level of a gene with atherosclerosis or atherogenesis, it is generally preferable to use a positive control (a subject or a sample from a subject, carrying such alteration and exhibiting syndromes characteristic of atherosclerosis or atherogenesis), and a negative control (a subject or a sample from a subject lacking the altered expression and syndromes characteristic of atherosclerosis or atherogenesis).

"The term "subject" includes, without limitation, humans and non-human primates, animal models, knock-out mice, livestock animals, companion animals, laboratory test animals, captive wild animals, reptiles and amphibians, fish, birds, and any other organism. A subject, regardless of whether it is a human or non-human organism may be referred to as an individual or subject.

The present invention, in some embodiments, uses hepatocytes. For the purpose of this document, the term "hepatocyte" refers to hepatocytes per se, obtained from a living mammal, and, in some embodiments, then cultured, and to hepatocyte-like cells derived from stem cells such as induced pluripotent stem cells.

EXAMPLES

The present examples include many numerical parameters, such as concentrations and incubation times and temperatures, among others. These numerical parameters are for exemplary purposes only and the scope of the appended claim should not be limited to the stated numerical values unless explicitly required by the claim.

Example 1

Simultaneous Measurement of Cholesterol Flux Between Cholesterol-Loaded, $^3$H-Cholesterol-Labeled J774 Cells and Target HepG2 Hepatocytes in a Transwell-Clear™ Insert.

Step 1, Preparation of Cell Cultures:

J774 cells were seeded at a density of 8,000 cells per cm$^2$ in 1 mL of Dulbecco's minimal essential medium (DMEM, high glucose) and supplemented with 10% fetal bovine serum (FBS) and 1% penicillin/streptomycin in standard 12-well (3.8 cm$^2$) flat bottom plates (Corning).

Transwell-Clear™ 12-well plates (Corning, cat. #3642), each consisting of 12 cylindrical cell culture inserts (1.12 cm$^2$ insert/well) were bathed with 2 mL Eagle's minimal essential medium (EMEM, low glucose) distributed as follows: 0.5 mL in the insert and 1.5 mL in the well. Loaded plates were pre-incubated in an incubator at 37° C. with 5% $CO_2$ for 30-45 min without cells in order to improve later cell attachment and maximize cell spreading on the insert membrane during cell culture. After pre-incubation, the media was removed. The wells of the Transwell plates were then filled with 1.5 mL of EMEM (low glucose) supplemented with 10% FBS and 1% penicillin/streptomycin and HepG2 cells were seeded at a density of 60,000 cells per cm$^2$ in 0.5 mL EMEM (low glucose) supplemented with 10% FBS and 1% penicillin/streptomycin on each insert.

Step 2, Incubation of J774 and HepG2 Cell Cultures:

Following seeding in plates or inserts, both cell types were placed in a cell incubator at 37° C. filled with humidified air and 5% $CO_2$ and incubated for 72 h.

Step 3, Cholesterol Loading and Labeling of J774 Cells:

Following the 72-hour incubation and achieving a J774 cell confluence of 70-80%, the J774 cells were washed with 1 mL per well of PBS at 20° C. After the wash, 1 mL of Labeling Medium was added to each well. The Labeling Medium contained: 1% FBS, 1% penicillin/streptomycin, 2 µCi/mL of $^3$H-cholesterol (Perkin-Elmer, NET139005MC), 50 µg protein/mL of acetylated LDL (acLDL) and DMEM (high glucose). The cells were then incubated for 24 hr at 37° C. in a cell incubator filled with humidified air and 5% $CO_2$. One plate served as a reference to determine the labeled-cholesterol level in cells prior to co-culture assay. This plate did not undergo cholesterol transport assays in contact with HepG2 cells and was used to monitor successful and constant labeling of J774 cells.

Preparation of Acetylated Low Density Lipoprotein:

Acetylated low-density lipoprotein (acLDL) is prepared by reaction with acetic anhydride according to a published protocol (Lougheed et al., 1999) and acLDL are stored in the dark at 4° C. for a maximum of one (1) month.

Step 4, Refresh HepG2 Culture Medium:

Following the 72-hour incubation, the culture medium was removed from HepG2 cells grown on the insert membrane and replaced with 2 mL of fresh EMEM (low glucose) supplemented with 10% FBS and 1% penicillin/streptomycin. The cells were then incubated for an additional 24 hours at 37° C. in an incubator filled with humidified air and 5% $CO_2$.

Step 5, Removal of Labeling Medium and Treatment:

Following the 24-hour incubation of J774 cells, the labeling medium was removed from the plates and discarded. The cells were then washed with 1 mL of phosphate-buffered saline (PBS) at 20° C. and replaced with Equilibration Medium containing: DMEM (high glucose), 0.2% Bovine Serum Albumin (BSA) (low endotoxin, fatty acid-free, Sigma, cat. #A8806) and the appropriate Treatment under study. The J774 culture was then incubated for 24 hours.

Treatment of Cells Before the Co-culture Assay.

J774 cells ongoing the $^3$H-cholesterol equilibration phase and/or HepG2 cells before co-culture can be treated by various means. Pharmacological agent is diluted in the appropriate culture medium with 0.2% BSA and vehicle (solvent) is tested in parallel. Modulation of gene expression is also accomplished at this step, by transfection of siRNA according to the manufacturer's protocol, and a control non-silencing RNA is tested in parallel.

Step 6, Co-Culture Assay:

After 24 hour of incubation, equilibration medium from J774 culture and culture medium from HepG2 cells were discarded. Cells were washed with 1 mL (J774) or 2 mL (HepG2) of PBS at 20° C. and the wash medium discarded. Transwell inserts containing HepG2 cells were removed and transferred to each well containing the J774 culture. 2 mL of co-culture media (DMEM without phenol red, high glucose, 4.5 g/L) were added to each well. The resulting co-culture system was incubated in a cell incubator at 37° C. for 24 hours.

Addition of Cholesterol Acceptors and Treatments in Co-Culture Medium:

Co-culture medium was incubated with the co-cultures alone to estimate background flux in the system or supplemented with Chol acceptors, such as serum, apoB-depleted serum, apolipoprotein A-I, HDL or LDL. In experiments aiming at determining parameters of cholesterol flux, a dose-response was established with 0.125%-4% human serum (and the corresponding 0.175%-5.6% apoB-depleted serum), 2.5-100 μg protein/ml human apoA-I, 5-300 μg protein/ml human HDL and 2.5-300 μg protein/ml human LDL. In experiments aiming at showing modulation of Chol flux by pharmacological or biological treatments of cells before or during the co-culture, a fixed dose of acceptor was tested, which was selected to avoid saturation of the efflux and influx values, based on association constants ($k_A$) data, and to allow sufficient signal to be detected over the background values. Typically, human serum was used at 0.25%, while apoB-depleted serum was used at 0.5%. If a pharmacological agent was solubilized in an organic solvent, such as DMSO or ethanol, the corresponding dose of solvent was tested in co-culture media alone and in co-culture medium with acceptors.

Step 7, Harvesting of Co-Culture Components:

Following the 24-hour incubation of the co-culture system, 2 mL of co-culture medium from each well were transferred to a 96 deep-well plate (VWR, cat.# P-DW-20-C), to collect media from plates. The Transwell insert was transferred to a clean 12-well plate to allow washing both cell types separately with 2 times 2 mL of PBS at room temperature.

Step 8, Processing of Co-Culture Medium:

The co-culture medium in 96-deep well plates was centrifuged at 124×g for 7 min to pellet cell debris and detached cells. A 0.5 mL aliquot of co-culture medium from each well was transferred to a 20 mL vial and 15 mL of liquid scintillation cocktail (Ecolite, MP Bio, cat.#882475) were added. Each vial was vortexed for 12 sec and left to rest for at least an hour at room temperature prior to counting with a β-counter. 96-deep well plates containing remaining co-culture medium were sealed with parafilm and stored at 4° C. for further analysis, if required.

Step 9, Processing of Co-Culture J774 Cells:

0.5 mL of NaOH 0.1 N was added to each well containing J774 cells. Cells, from each well, were solubilized with a glass pipette and the cell lysate was added to a 20-mL vial. Wells were then washed with additional 0.5 mL NaOH 0.1 N and the wash added to the 20-mL vial containing the lysate and homogenized. 15 ml of liquid scintillation cocktail (Ecolite, MP Bio, cat.#882475) were added to each 20 mL vial and each vortexed for 12 sec and left to rest for at least 1 hour at room temperature prior to counting with a β-counter.

Step 10, Processing of Co-Culture HepG2 Cells:

Inserts were allowed to dry and the membrane was detached from the insert plastic support with a razor blade. The membranes were transferred to a 20-mL vial and 15 mL of liquid scintillation cocktail (Ecolite, MP Bio, cat.#882475) added. Each vial was vortexed for 12 sec and allowed to rest for at least 1 hour at room temperature prior to counting with a β-counter.

Step 11, Measurement of $^3$H-Cholesterol in Co-Culture Components:

$^3$H-Chol tracer content in co-culture medium, J774 cell lysate and insert membrane with HepG2 cells were estimated with a β-counter (Tricarb, Perkin-Elmer) as counts per minute (cpm). A correction factor of 1.1 was applied for medium samples as determined from the effect of 0.5 ml culture medium in 15 ml scintillation cocktail compared to water.

Step 12, Calculation of Chol Efflux and Uptake in the Co-Culture System:

Assuming that radioactivity in HepG2 cells on the insert membrane has undergone efflux in the first place, % Chol efflux (% Efflux) was calculated as:

$$[(\text{cpm in co-culture medium*}) + (\text{cpm on insert membrane with cells})/(\text{total cpm in co-culture system})] \times 100\%.$$

While % Chol uptake (% Uptake) was calculated as:

$$[(\text{cpm on insert membrane})/(\text{total cpm in co-culture system**})] \times 100\%.$$

* cpm in co-culture medium is corrected by a recovery factor of 4, as 0.5 mL/2 mL have been counted.

** total cpm in co-culture system equals the sum of cpm in J774 cell lysate, cpm in co-culture medium (corrected) and cpm counts from the insert membrane with HepG2 cells.

Specific Chol flux induced by an acceptor in co-culture medium can be obtained by subtracting background values obtained with basal medium (without acceptors) to describe the specific effect of treatments on acceptor-dependent fluxes:

$$\text{Specific Efflux (\%)} = \% \text{ Efflux with acceptor} - \% \text{ Efflux without acceptor (basal medium)}.$$

$$\text{Specific Uptake (\%)} = \% \text{ Uptake with acceptor} - \% \text{ Uptake without acceptor (basal medium)}.$$

Thus, Specific Uptake or Efflux=Total Uptake or Efflux−Basal Uptake or Efflux.

This is done for each treatment or control.

Example 2

Figure 1B:
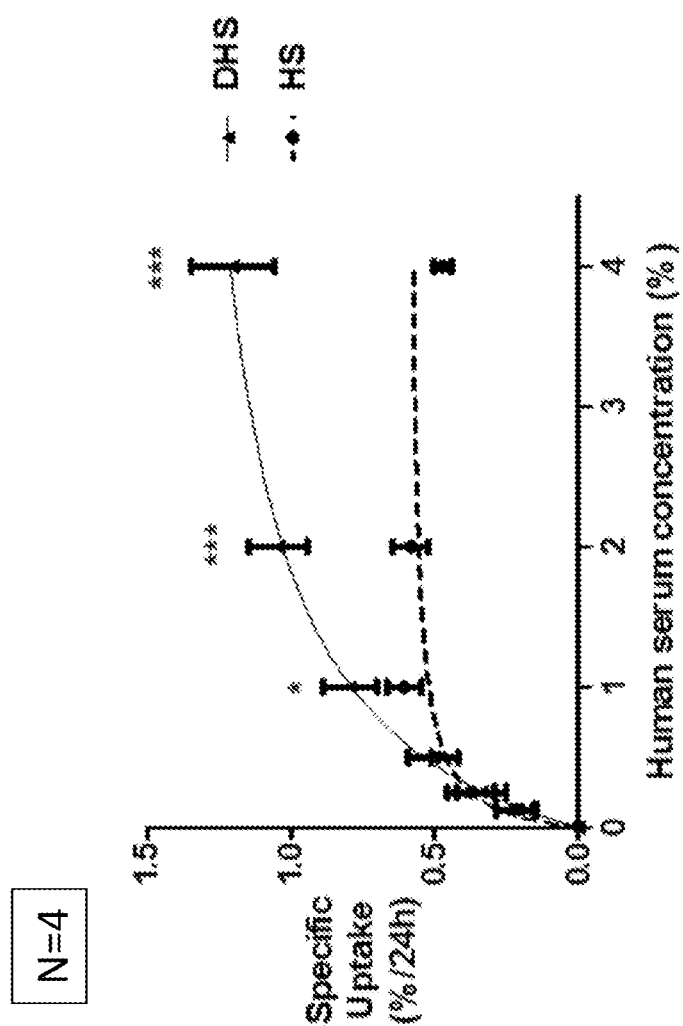
Figure 6C:
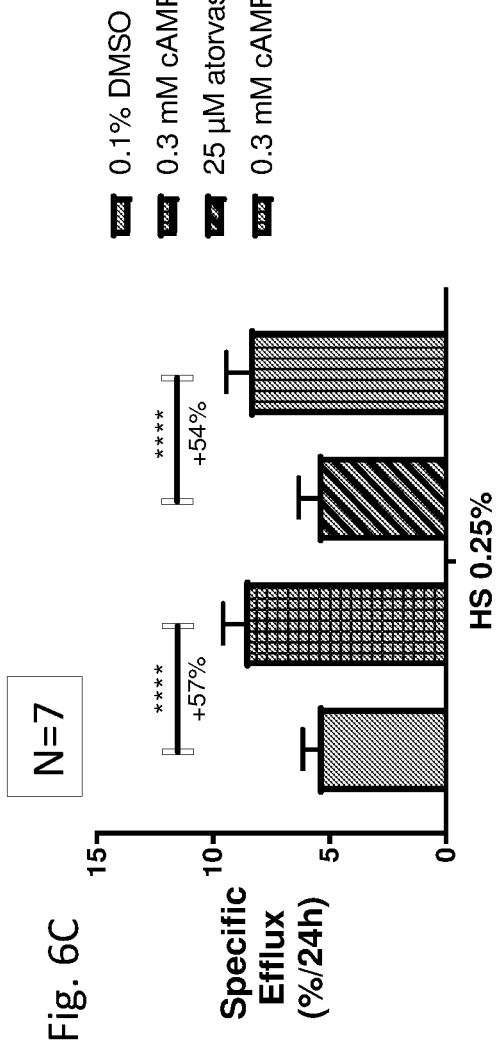
Figure 6D:
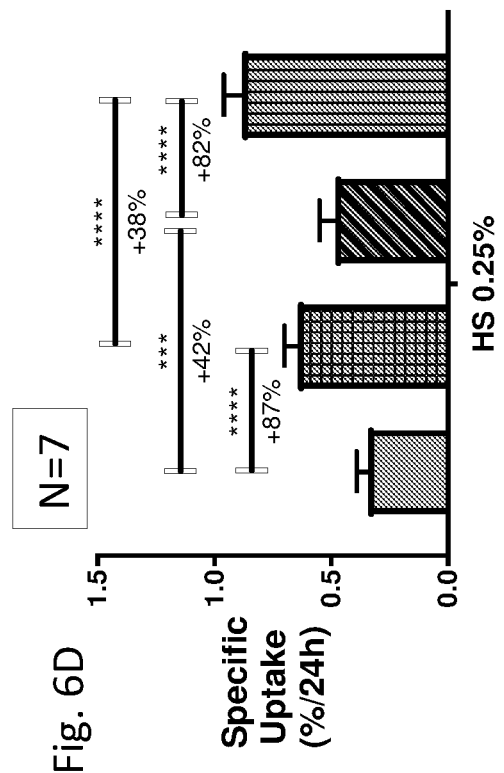

Human Serums (Complete and apoB-Depleted) were Tested as Chol acceptors in the co-culture system for 24 hours. Complete serum was tested at 0.125, 0.25, 0.5, 1.0, 2.0 and 4.0% (v/v) and apoB-depleted serum at the corresponding doses of 0.175, 0.35, 0.7, 1.4, 2.8 and 5.6%, taking into account a 1.4-fold dilution factor. Results are shown in FIGS. 1A and 1B. Specific Chol Efflux from J774 macrophages towards co-culture medium acceptors and Specific Chol Uptake into HepG2 hepatocytes increased as a function of serum dose and were obtained simultaneously during a 24 h co-culture experiment. Both human serum (HS) and apoB-depleted human serum (DHS) show saturation of efflux and uptake at the maximal dose tested. Incubation with HS resulted in significantly higher efflux compared to DHS, while HS drives lower Specific Chol Uptake compared to DHS. Saturation of the Specific Chol Uptake for HS occurs at lower doses, which suggest higher affinity of the receptor involved.

Additionally, HS has a good target-to-background ratio vs. co-culture medium alone in efflux and uptake measurements. We determined the lowest dose that can be used to monitor both flux components to be 0.125% HS (equivalent to 0.175% DHS).

Example 3

Purified human HDL, human apoA-I and human LDL were tested as Chol acceptors in the co-culture system for 24 hours. HDL were tested at 5, 15, 30, 50, 90, 150, 200 and 300 μg protein/ml, apoA-I at 2.5, 5, 10, 50 and 100 μg protein/mL and LDL at 2.5, 5, 15, 30, 50, 90, 150, 200 and 300 μg protein/mL. HDL and apoA-I acceptors provide an efficient vehicle for Chol flux compared to isolated human LDL. At the highest dose tested for the 3 acceptors (100 μg/ml), Specific Chol Efflux was higher for HDL and apoA-I compared to LDL. Specific Chol Uptake was saturated at doses >0.1 μg/ml for LDL and maximal Specific Chol Uptake for LDL was markedly lower than Specific Chol Uptake with HDL or apoA-I.

Example 4

Using the data obtained from dose-response curves for each type of acceptor in co-culture for 24 h, parameters describing Chol fluxes were obtained by non-linear regression fitting to a one-site binding model with GraphPad Prism 5 software. Results are shown in FIGS. 2A to 2D and in Table 1. More specifically, for Table 1, this Table lists parameters of specific Chol efflux and Chol uptake with various Chol acceptors in standard co-culture conditions. Based on the dose-response curves with different acceptors, we determined the affinity constants ($k_D$) for the fluxes as % v/v (serum) or μg protein/ml acceptor and maximal Specific Chol Efflux and Specific Chol Uptake ($B_{max}$) Non-linear regression models were created in GraphPad Prism 5.0 assuming a single site and saturation of the curve with the sole constrain that $B_{max}$ and $K_D$ were >0. All models were highly significant. These parameters provide reference values for samples prepared from normolipidemic healthy volunteers (human serum, purified HDL, apoA-I and LDL) and allow selection of acceptor concentration for single-dose experiments. ApoA-I: human apolipoprotein A-I; HDL: total human high-density lipoproteins; LDL: human low-density lipoproteins. The affinity constant ($k_A$) and the maximal transport ($B_{max}$) for Specific Chol Efflux and Specific Chol Uptake were expressed in concentration units (μg/mL or % v/v) for the $k_A$ or in % flux for the $B_{max}$. These parameters help to select doses of acceptors that avoid saturation of the system and allow measuring modulation of the Specific Chol Efflux and Specific Chol Uptake by various treatments, working at or near the $k_A$. Typically, for single-dose experiments in the examples, HS was used at 0.25%, DHS at 0.5% and HDL at 15 μg/mL.

TABLE 1

|  | Complete human serum (HS) N = 4 | Depleted human serum (DHS) N = 4 | Human apolipoprotein A-I (ApoA-I) N = 3 | Isolated human HDL N = 3 | Isolated human LDL N = 3 |
|---|---|---|---|---|---|
|  | $k_A$ (affinity constant), % serum or μg protein/mL | | | | |
| Specific Efflux | 1.03 ± 0.08 | 1.71 ± 0.16 | 7.2 ± 1.4 | 171.7 ± 30.6 | 190.3 ± 28.7 |
| Specific Uptake | 0.15 ± 0.03 | 0.86 ± 0.11 | 7.0 ± 1.0 | 40.3 ± 5.2 | <0.1 |
|  | $B_{max}$ (maximal flux), % | | | | |
| Specific Efflux | 31.7 ± 1.0 | 31.8 ± 1.5 | 15.9 ± 0.9 | 43.4 ± 3.9 | 20.1 ± 1.7 |
| Specific Uptake | 0.60 ± 0.03 | 1.47 ± 0.07 | 0.83 ± 0.03 | 1.25 ± 0.05 | 0.11 ± 0.01 |

Example 5

Human complete serum was used as an acceptor in the co-culture assay for 24 hours. At the end of co-culture, following selective precipitation of apoB-containing lipoproteins with sodium phosphotungstate/magnesium chloride reagent (Warnick et al., 1982), Chol tracer was distributed between the pellet (VLDL and LDL) and the supernatant (HDL and serum proteins). Results are shown in Table 2 below, which details the distribution of radioactive labeled Chol in human serum lipoproteins following co-culture of macrophages and hepatocytes. Human complete serum was diluted at increasing concentrations (0-4%) in culture medium and incubated for 24 hours in the co-culture system. Chol tracer in VLDL/LDL vs. HDL was quantified by precipitating apoB-containing lipoproteins from the co-culture medium with sodium phosphotungstate/magnesium chloride, while the supernatant contained HDL-enriched serum. Chol tracer counts were measured by beta counting of aliquots from the supernatant or the re-suspended pellets. The 0% serum dose corresponds to the basal co-culture medium incubated for 24 hours. Chol tracer was distributed in both apoB-containing lipoproteins and HDL at any dose, the majority of which being in apoB-containing lipoproteins, respectful of the Chol content in VLDL/LDL vs. HDL, as indicated in the Table. Non-HDL-C: Chol content in LDL and VLDL. At the lowest dose tested (0.125% HS), 36.3±18.0% of the Chol tracer was found in the supernatant, while increasing the serum dose favored the exchange of Chol tracer and reduced the fraction in the supernatant to 15.4±2.2% and increased it in VLDL/LDL to 85%. Thus, Chol uptake pathways involving LDL and HDL may be traced from the co-culture medium.

TABLE 2

| | Human serum concentration in medium (% v/v) | | | | | |
|---|---|---|---|---|---|---|
| | 0.125 | 0.25 | 0.5 | 1.0 | 2.0 | 4.0 |
| 3H-cholesterol in supernatant (% total) | 36.3 (18) | 36.7 (9) | 32.9 (17) | 24.3 (12) | 17.5 (1.5) | 15.4 (2.2) |
| 3H-cholesterol in apoB pellet (% total) | 63.7 (18) | 63.3 (9) | 67.1 (17) | 75.6 (12) | 82.5 (1.5) | 84.6 (2.2) |
| HDL-C (µg/mL) | 0.52 | 1.03 | 2.07 | 4.13 | 8.28 | 16.55 |
| Non-HDL-C (µg/mL) | 1.47 | 2.95 | 5.90 | 11.80 | 23.59 | 47.18 |

Example 6

Human serums (complete and apoB-depleted) were used as acceptors in the co-culture assay for 24 hours following pre-treatment of J774 macrophages with 10 µM TO901317, an LXR agonist that increases ABCA1 and ABCG1-mediated Chol efflux from cells (Zanotti et al., 2008) or vehicle (DMSO). Results are shown in FIGS. 3A and 3B. TO901317 increased significantly Chol flux in co-culture, as increased Specific Chol Efflux was simultaneously accompanied by increased Specific Chol Uptake from DHS and HS in co-culture. Thus, activation of macrophage LXR allows increased Chol flux to the hepatocytes.

Example 7

Human serums (complete and apoB-depleted) were used as acceptors in the co-culture assay for 24 hours following pre-treatment of hepatocytes with 10 µM atorvastatin, 10 µM mevastatin or vehicle (ethanol or DMSO). Atorvastatin and mevastatin are 3-hydroxy-3-methylglutaryl-CoA reductase inhibitors that cause increased LDL receptor expression in hepatocytes by a transcriptional mechanism (Dong et al., 2011). Results are shown in FIGS. 4A to 4B. Both statins had no effect on Chol Efflux to human serum, but both increased hepatic Chol Uptake with complete human serum, suggesting that LDL catabolism is enhanced by the LDLR pathway in this setting. Statins had a reduced effect on Chol Uptake from apoB-depleted serum compared to complete serum. Atorvastatin increased Chol Uptake directly from human LDL in agreement with its effect from complete serum.

Example 8

Human complete serum was used as an acceptor in the co-culture assay for 24 hours in presence of 10 nM purified human PCSK9 gain-of-function D374Y mutant protein. This mutant has high affinity for cellular LDLR and causes its degradation in human hepatocytes and severe hypercholesterolemia due to impaired LDL uptake (Naoumova et al., 2005). Results are shown in FIGS. 5A and 5B. PCSK9 D374Y markedly reduced Specific Chol Uptake from complete human serum, while it had no effect on Specific Chol Efflux. Thus, LDL receptors are involved in uptake of cholesterol from complete HS.

Example 9

Human LDL were used as acceptors in the co-culture assay for 24 hours following pre-treatment of HepG2 hepatic cells with 25 µM atorvastatin or vehicle. Results are shown in FIGS. 4C and 4D. While atorvastatin did not modify Chol Efflux from macrophages, it increased significantly Chol Uptake from human LDL in hepatic cells.

Example 10

Human serum (complete and apoB-depleted) were used as acceptors in the co-culture assay for 24 hours following pre-treatment of macrophages with 300 µM cyclic AMP (cAMP, in water as vehicle) or pre-treatment of HepG2 cells with 25 µM atorvastatin (in ethanol as vehicle) or both treatments on the respective cell line. cAMP is a transcriptional inducer of ABCA1 and ABCG1 transporters in macrophages (Huang et al., 2001). Results are shown in FIGS. 6A to 6D. cAMP treatment of J774 macrophages increased Chol Efflux to both complete and apoB-depleted serum and this resulted in increased Chol Uptake in HepG2 cells. Atorvastatin treatment of hepatic cells, as expected from Example 7, did not affect Chol Efflux, but increased Chol Uptake in presence of complete human serum containing VLDL and LDL. Combination of the two treatments before setting up the co-culture produced additive effects on Chol Uptake with complete human serum, but not with apoB-depleted serum.

Example 11

Figure 7A:
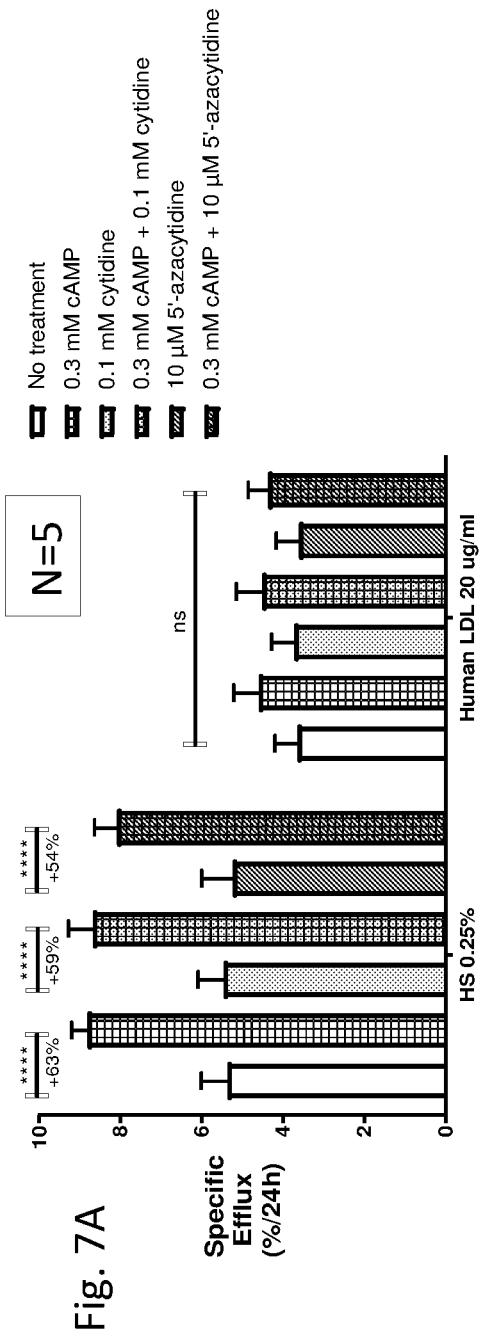
FIGS. 7A and 7B illustrate the effect of J774 macrophage treatment with cyclic AMP (cAMP) and/or HepG2 cells with 5'-azacytidine on Chol flux in co-culture. Before the co-culture assay, J774 macrophages were treated overnight with 300 µM 8-bromo-cyclic AMP to induce cholesterol transporters of the ABC family, and/or HepG2 cells were treated overnight with 10 µM 5'-azacytidine, a DNA methyltransferase inhibitor which upregulates LDL receptor expression in hepatocytes. Co-culture was performed for 24 hours in presence of representative doses of complete human serum or human LDL. Specific Chol Efflux and Specific Chol Uptake were determined by beta counting of aliquots from co-culture medium, J774 macrophage lysates and insert membrane HepG2 cells. cAMP increased Specific Chol Efflux in presence of complete human serum, but not LDL (FIG. 7A). Treating HepG2 cells with 5'-azacytidine did not modulate Specific Chol Efflux in presence or absence of macrophage cAMP treatment, as expected (FIG. 7A). However, treating HepG2 cells with 5'-azacytidine increased Specific Chol Uptake from both complete human serum (containing VLDL and LDL) and human LDL (FIG. 7B) and had an additive effect to cAMP treatment on Specific Chol Uptake from complete serum (FIG. 7B), but not from human LDL. Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). HS: human serum.
Figure 7B:
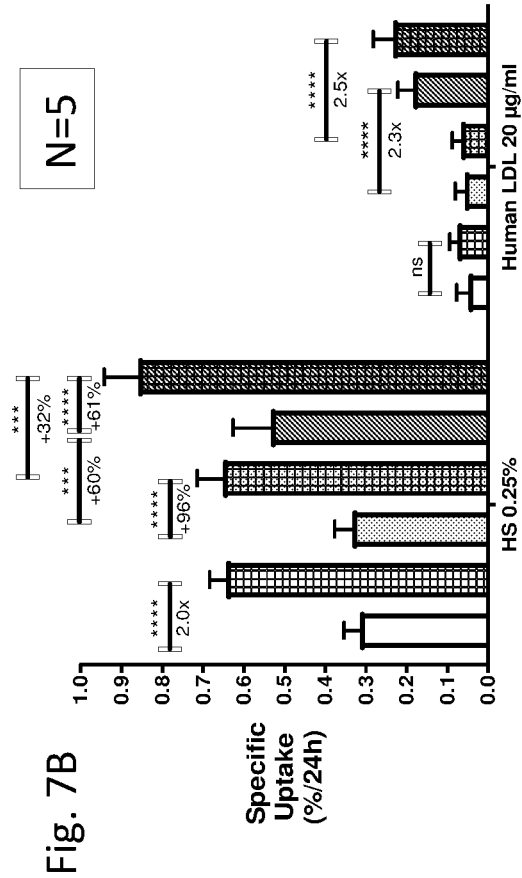
Figures 8C, 8D:
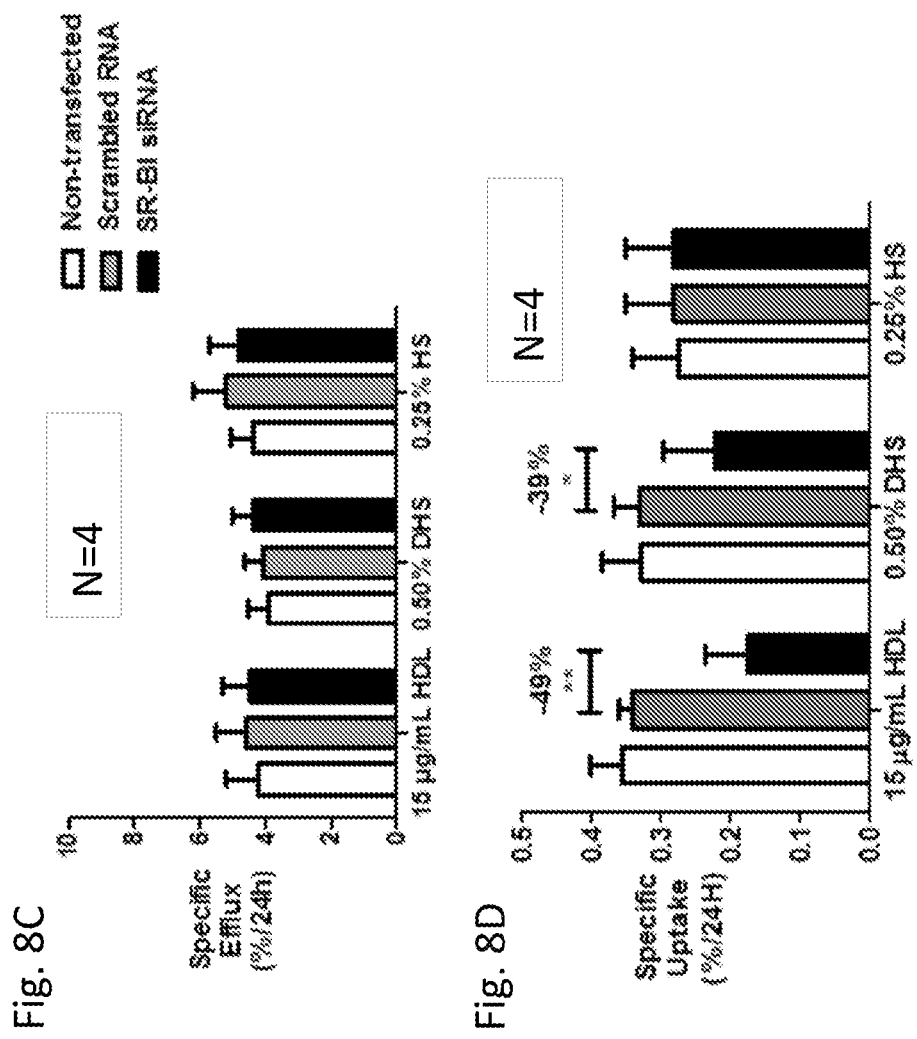

Human serum (complete and apoB-depleted) were used as acceptors in the co-culture assay for 24 hours following pre-treatment of J774 macrophages with 300 µM cyclic AMP (cAMP, in water as vehicle) or pre-treatment of HepG2 hepatic cells with 10 µM 5'-azacytidine (and cytidine as control in water) or both treatments on the respective cell line. Results are shown in FIGS. 7A and 7B. 5'-azacytidine is an inhibitor of DNA methyltransferase that represses PCSK9 mRNA and protein expression, while inducing LDL receptor expression at the mRNA and protein level (Poirier et al. 2015). cAMP treatment of macrophages increased Chol Efflux to both complete and apoB-depleted serum, as expected from Example 10, and this resulted in increased Chol Uptake in hepatic cells. 5'-azacytidine treatment of hepatic cells did not affect Chol Efflux, but increased Chol Uptake in presence of complete human serum containing LDL and VLDL, and not from apoB-depleted serum. Combination of the two treatments before setting up the co-culture produced additive effects on Chol Uptake with complete human serum, but not with apoB-depleted serum, as for the cAMP-atorvastatin combination of Example 10.

Example 12

Human LDL were used as acceptors in the co-culture assay for 24 hours following pre-treatment of J774 macrophages with 300 µM cyclic AMP (cAMP, in water as vehicle) or pre-treatment of HepG2 hepatic cells with 10 µM 5'-azacytidine (or cytidine as control in water) or both treatments on the respective cell line. Results are shown in FIGS. 7A and 7B. 5'-azacytidine is an inhibitor of DNA methyltransferase that represses PCSK9 mRNA and protein expression, while inducing LDL receptor expression at the mRNA and protein level (Poirier et al. 2015). cAMP treatment of macrophages did not increase Chol Efflux and Chol Uptake in hepatic cells in presence of human LDL. 5'-azacytidine treatment of hepatic cells did not affect Chol Efflux, but increased Chol Uptake in presence or absence of cAMP treatment of macrophages. Combination of the two treatments before setting up the co-culture did not produce additive effects, as expected from the selective effect of 5'-azacytidine on Chol Uptake from LDL.

Example 13

Human serum (complete and apoB-depleted) and purified human HDL were used as acceptors in the co-culture assay for 24 hours following silencing RNA (siRNA)-mediated knock-down of the hepatic HDL receptor SR-BI. siRNA against SR-BI (6 pmol/well, Thermo-Fisher #1299001) and a scrambled RNA negative control were transfected twice, 48 and 24 hours before the co-culture assay. Non-transfected cells were tested in parallel. Western blotting was performed in parallel on a duplicate series of HepG2 cells grown on inserts to show that SR-BI knock-down was obtained before (−76%) and at the end (−87%) of the co-culture phase. Results are shown in FIGS. 8A to 8D. SR-BI knock-down reduced Specific Chol Uptake from purified human HDL (−49%) and apoB-depleted serum (−39%), but not from complete serum, showing its direct involvement in HDL-cholesterol uptake and limited impact on LDL-cholesterol uptake.

Example 14

Figures 9A, 9B:
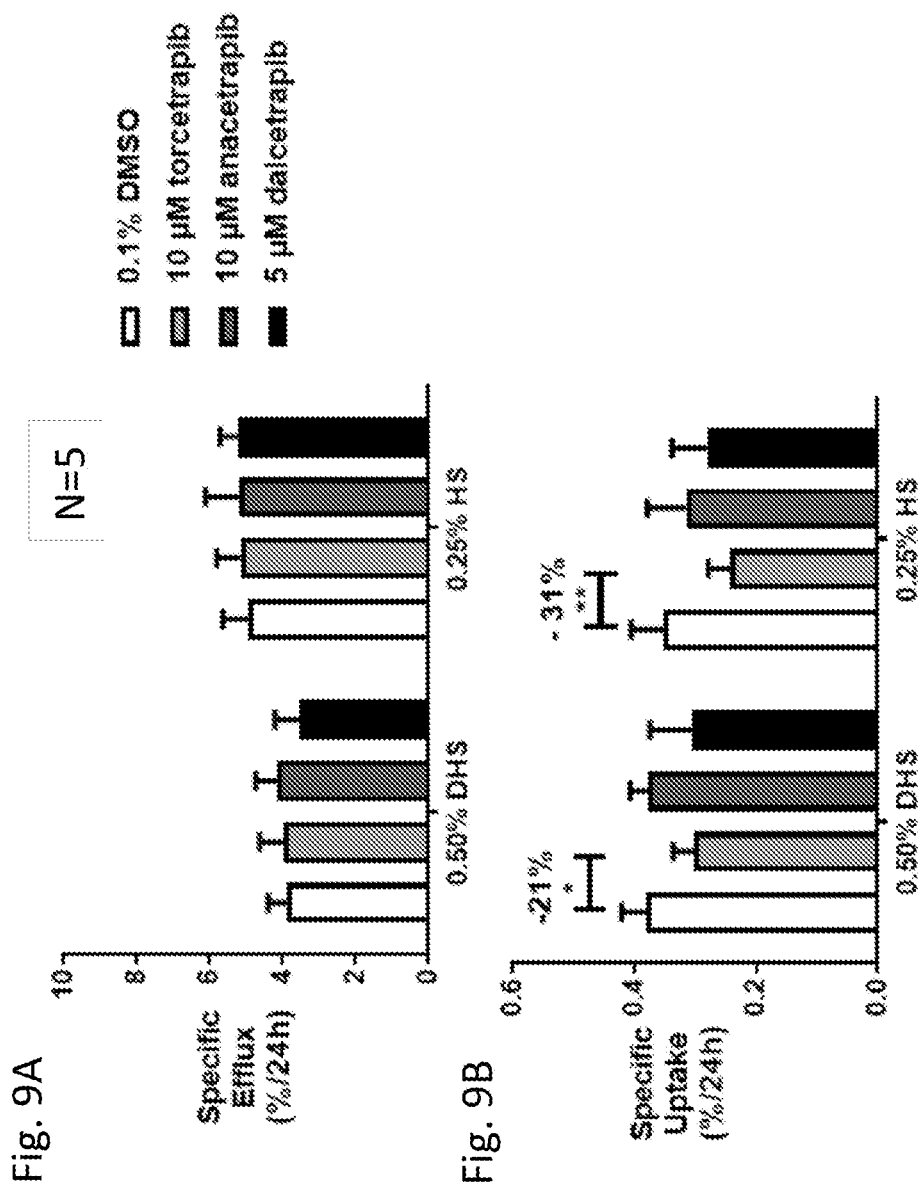
FIGS. 9A and 9B illustrate the effect of CETP inhibitors on HepG2 cells and during co-culture on Chol flux in co-culture. Before the co-culture assay, HepG2 cells were treated overnight with 10 µM torcetrapib, 10 µM anacetrapib or 5 µM dalcetrapib, CETP inhibitors that block transfer of HDL-derived cholesteryl esters to apoB-containing lipoproteins. Co-culture was performed for 24 hours in presence of representative doses of human serum (complete and apoB-depleted) and in presence of the same doses of inhibitors or vehicle. Specific Chol Efflux and Uptake were determined by beta counting of aliquots from co-culture medium, J774 macrophage lysates and insert membrane HepG2 cells. Torcetrapib did not affect Specific Efflux (FIG. 9A), but reduced Specific Uptake (FIG. 9B) in presence of human serum (complete and apoB-depleted) suggesting that reduction of Chol transfer to LDL and the corresponding accumulation in HDL do not favor hepatic uptake from HDL either in complete serum or HDL-enriched in apoB-depleted serum. Specific Efflux (%)=(% Efflux in presence of serum−% Efflux without acceptor [basal medium]), where % Efflux=(medium counts+hepatic cell counts)/(total counts in co-culture). Specific Uptake (%)=(% Uptake in presence of serum−% Uptake without acceptor [basal medium]), where % Uptake=(hepatic cell counts)/(total counts in co-culture). Tor: torcetrapib; Ana: anacetrapib; Dal: dalcetrapib. HS: human serum; DHS: apoB-depleted human serum, and FIG. 10, in a schematic view, illustrates an assay system in accordance with an embodiment of the present invention.

Human serums (complete and apoB-depleted) were used as acceptors in the co-culture assay for 24 hours following pre-treatment of HepG2 hepatocytes with the cholesteryl esters transfer protein (CETP) inhibitors: 10 µM torcetrapib (Dalvie et al., 2008), 10 µM anacetrapib (Krishna et al., 2009) or 5 µM dalcetrapib (2010) or the vehicle (DMSO). Treatments were also maintained during the co-culture, as active CETP is also brought in the co-culture by human serum. Results are shown in FIGS. 9A and 9B. The potent CETP inhibitor torcetrapib reduced hepatic Specific Chol Uptake by 31% with complete serum and by 21% with apoB-depleted serum, suggesting that it reduces uptake from HDL particles in the first place, despite its use as a molecule to block transfer of Chol to apoB-containing lipoproteins which could result in higher amounts of tracer in HDL.

Although the present invention has been described hereinabove by way of preferred embodiments thereof, it can be modified, without departing from the spirit and nature of the subject invention as defined in the appended claim.

REFERENCES (2010). Dalcetrapib: JTT 705; JTT-705; R 1658; R1658; RG1658; RO 4607381; R04607381. Drugs in R&D 10, 33-36.

Amar, M. J., D'Souza, W., Turner, S., Demosky, S., Sviridov, D., Stonik, J., Luchoomun, J., Voogt, J., Hellerstein, M., Sviridov, D., et al. (2010). 5A apolipoprotein mimetic peptide promotes cholesterol efflux and reduces atherosclerosis in mice. The Journal of pharmacology and experimental therapeutics 334, 634-641.

Amar, M. J., Sakurai, T., Sakurai-lkuta, A., Sviridov, D., Freeman, L., Ahsan, L., and Remaley, A. T. (2015). A novel apolipoprotein C-II mimetic peptide that activates lipoprotein lipase and decreases serum triglycerides in apolipoprotein E-knockout mice. The Journal of pharmacology and experimental therapeutics 352, 227-235.

Asztalos, B. F., de la Llera-Moya, M., Dallal, G. E., Horvath, K. V., Schaefer, E. J., and Rothblat, G. H. (2005) Differential effects of HDL subpopulations on cellular ABCA1- and SR-BI-mediated cholesterol efflux. Journal of lipid research 46:2246-2253.

Dalvie, D., Chen, W., Zhang, C., Vaz, A. D., Smolarek, T. A., Cox, L. M., Lin, J., and Obach, R. S. (2008). Pharmacokinetics, metabolism, and excretion of torcetrapib, a cholesteryl ester transfer protein inhibitor, in humans. Drug metabolism and disposition: the biological fate of chemicals 36, 2185-2198.

Di Bartolo, B. A., Nicholls, S. J., Bao, S., Rye, K. A., Heather, A. K., Barter, P. J., and Bursill, C. (2011). The apolipoprotein A-I mimetic peptide ETC-642 exhibits anti-inflammatory properties that are comparable to high density lipoproteins. Atherosclerosis 217, 395-400.

Dong, B., Wu, M., Cao, A., Li, H., and Liu, J. (2011). Suppression of Idol expression is an additional mechanism underlying statin-induced up-regulation of hepatic LDL receptor expression. International journal of molecular medicine 27, 103-110.

Gautier, T., Masson, D., and Lagrost, L. (2016). The potential of cholesteryl ester transfer protein as a therapeutic target. Expert opinion on therapeutic targets 20, 47-59.

Hafiane, A., Bielicki, J. K., Johansson, J. O., and Genest, J. (2014). Apolipoprotein E derived HDL mimetic peptide ATI-5261 promotes nascent HDL formation and reverse cholesterol transport in vitro. Biochimica et biophysica acta 1842, 1498-1512.

Huang, Z. H., Lin, C. Y., Oram, J. F., Mazzone, T. (2001). Sterol efflux mediated by endogenous macrophage ApoE expression is independent of ABCA1. Arteriosclerosis thrombosis and vascular biology. 21, 2019-2025.

Krishna, R., Garg, A., Panebianco, D., Cote, J., Bergman, A. J., Van Hoydonck, P., Laethem, T., Van Dyck, K., Chen, J., Chavez-Eng, C., et al. (2009). Single-dose pharmacokinetics and pharmacodynamics of anacetrapib, a potent cholesteryl ester transfer protein (CETP) inhibitor, in healthy subjects. British journal of clinical pharmacology 68, 535-545.

Li, X. M., Tang, W. H., Mosior, M. K., Huang, Y., Wu, Y., Matter, W., Gao, V., Schmitt, D., Didonato, J. A., Fisher, E. A., et al. (2013). Paradoxical association of enhanced cholesterol efflux with increased incident cardiovascular risks. Arteriosclerosis, thrombosis, and vascular biology 33, 1696-1705.

Lougheed, M., Moore, E. D., Scriven, D. R., and Steinbrecher, U. P. (1999). Uptake of oxidized LDL by macrophages differs from that of acetyl LDL and leads to expansion of an acidic endolysosomal compartment. Arteriosclerosis, thrombosis, and vascular biology 19, 1881-1890.

Merlet, N., Busseuil, D., Mihalache-Avram, T., Mecteau, M., Shi, Y., Nachar, W., Brand, G., Brodeur, M. R., Charpentier, D., Rhainds, D., et al. (2016). HDL mimetic peptide CER-522 treatment regresses left ventricular diastolic dysfunction in cholesterol-fed rabbits. International journal of cardiology 215, 364-371.

Naoumova, R. P., Tosi, I., Patel, D., Neuwirth, C., Horswell, S. D., Marais, A. D., van Heyningen, C., and Soutar, A. K. (2005). Severe hypercholesterolemia in four British families with the D374Y mutation in the PCSK9 gene: long-term follow-up and treatment response. Arteriosclerosis, thrombosis, and vascular biology 25, 2654-2660.

Phillips, M. C. (2014). Molecular mechanisms of cellular cholesterol efflux. The Journal of biological chemistry 289, 24020-24029.

Poirier, S., Samami, S., Mamarbachi, M., Demers, A., Chang, T. Y., Vance, D. E., Hatch, G. M., Mayer, G. (2014). *The epigenetic drug 5-azacytidine interferes with cholesterol and lipid metabolism.* Journal of biological chemistry 289, 18736-18751.

Qin, S., Kamanna, V. S., Lai, J. H., Liu, T., Ganji, S. H., Zhang, L., Bachovchin, W. W., and Kashyap, M. L. (2012). Reverse D4F, an apolipoprotein-Al mimetic peptide, inhibits atherosclerosis in ApoE-null mice. Journal of cardiovascular pharmacology and therapeutics 17, 334-343.

Rothblat, G. H. (1974). Cholesteryl ester metabolism in tissue culture cells. I. Accumulation in Fu5AH rat hepatoma cells. Lipids 9, 526-535.

Schwartz, C. C., VandenBroek, J. M., and Cooper, P. S. (2004). Lipoprotein cholesteryl ester production, transfer, and output in vivo in humans. Journal of lipid research 45, 1594-1607.

Tanigawa, H., Billheimer, J. T., Tohyama, J., Zhang, Y., Rothblat, G., and Rader, D. J. (2007). Expression of cholesteryl ester transfer protein in mice promotes macrophage reverse cholesterol transport. Circulation 116, 1267-1273.

Tardif, J. C., Gregoire, J., L'Allier, P. L., Ibrahim, R., Lesperance, J., Heinonen, T. M., Kouz, S., Berry, C., Basser, R., Lavoie, M. A., et al. (2007). Effects of reconstituted high-density lipoprotein infusions on coronary atherosclerosis: a randomized controlled trial. Jama 297, 1675-1682.

Tardy, C., Goffinet, M., Boubekeur, N., Ackermann, R., Sy, G., Bluteau, A., Cholez, G., Keyserling, C., Lalwani, N., Paolini, J. F., et al. (2014). CER-001, a HDL-mimetic, stimulates the reverse lipid transport and atherosclerosis regression in high cholesterol diet-fed LDL-receptor deficient mice. Atherosclerosis 232, 110-118.

Tricoci, P., D'Andrea, D. M., Gurbel, P. A., Yao, Z., Cuchel, M., Winston, B., Schott, R., Weiss, R., Blazing, M. A., Cannon, L., et al. (2015). Infusion of Reconstituted High-Density Lipoprotein, CSL112, in Patients With Atherosclerosis: Safety and Pharmacokinetic Results From a Phase 2a Randomized Clinical Trial. Journal of the American Heart Association 4, e002171.

Turner, S., Voogt, J., Davidson, M., Glass, A., Killion, S., Decaris, J., Mohammed, H., Minehira, K., Boban, D., Murphy, E., et al. (2012). Measurement of reverse cholesterol transport pathways in humans: in vivo rates of free cholesterol efflux, esterification, and excretion. Journal of the American Heart Association 1, e001826.

Warnick, G. R., Mayfield, C., Benderson, J., Chen, J. S., and Albers, J. J. (1982). HDL cholesterol quantitation by phosphotungstate-Mg2+ and by dextran sulfate-Mn2+-polyethylene glycol precipitation, both with enzymic cholesterol assay compared with the lipid research method. American journal of clinical pathology 78, 718-723.

Zanoni, P., Khetarpal, S. A., Larach, D. B., Hancock-Cerutti, W. F., Millar, J. S., Cuchel, M., DerOhannessian, S., Kontush, A., Surendran, P., Saleheen, D., et al. (2016). Rare variant in scavenger receptor BI raises HDL cholesterol and increases risk of coronary heart disease. Science 351, 1166-1171.

Zanotti, I., Poti, F., Pedrelli, M., Favari, E., Moleri, E., Franceschini, G., Calabresi, L., and Bernini, F. (2008). The LXR agonist T0901317 promotes the reverse cholesterol transport from macrophages by increasing plasma efflux potential. Journal of lipid research 49, 954-960.

The invention claimed is:

1. An in vitro assay system for measuring cholesterol (Chol) transport, comprising:
macrophages; and
hepatocytes;
the macrophages and the hepatocytes being in a shared culture medium to allow Chol transport between the macrophages and the hepatocytes, wherein the macrophages and the hepatocytes are segregated from each other, wherein the assay system comprises a first and a second culture vessel, wherein the first and second culture vessels are adjacent to each other, wherein a porous membrane is provided between the first and second culture vessels, and wherein the hepatocytes are supported on the membrane, wherein at least one of the macrophages and culture medium includes labeled Chol, wherein the second culture vessel is provided above the first culture vessel, and wherein the macrophages express a transporter protein that mediates Chol efflux from the macrophages into the culture medium, and wherein the culture medium contains a PCSK9 antagonist or a cholesteryl esters transfer protein (CETP) inhibitor and wherein the macrophages are contained and confined in the first cell culture vessel, the hepatocytes are contained and confined in the second cell culture vessel, and the culture medium permeates the first and second cell culture vessels with the first and second culture vessels in a fluid communication relationship with each other so that the culture medium can diffuse between the first and second cell culture vessels.

2. The in vitro assay system as defined in claim 1, wherein the macrophages include cells selected from the group consisting of a mouse macrophage cell line, a human macrophage cell line, a monocyte-derived cell line, a primary culture of macrophages, a genetically modified macrophage cell line or a macrophage-like cell derived from induced pluripotent stem cells.

3. The in vitro assay system as defined in claim 2, wherein the macrophages include cells selected from the group consisting of murine cell lines J774A.1 (American Type Culture Collection (ATCC) TIB-67), J774.2 (Sigma-Aldrich 85011428), LADMAC (ATCC CRL-2420), RAW 264.7 (ATCC TIB-71), RAW 309 (ATCC TIB-69), P388D1 (ATCC CCL-46), WEHI-265.1 (ATCC TIB-204), and WEHI-274 (ATCC CRL-1679), human cell lines THP-1 (ATCC TIB-202), JM1 (ATCC CRL-10423), KG-1 (ATCC CCL-246), U937 (ATCC CRL-1593.2), AML-193 (ATCC CRL-9589), MD (ATCC CRL-9850), and SC (ATCC CRL-9855), and macrophages derived from tissue resident macrophages, human induced pluripotent stem cells, monocyte cell lines, WEHi cells, THP-1 cells, primary monocytic cells, peripheral blood monocytic cells, $CD14^+$ cells.

4. The in vitro assay system as defined in claim 1, wherein the hepatocytes express a protein that mediates Chol uptake from the culture medium into the hepatocytes, and wherein the protein that mediates Chol uptake from the culture medium into the hepatocytes includes at least one of a low-density lipoprotein receptor (LDLR), scavenger receptor class B, type 1 (SR-B1), CD36 or LDLR-related protein-1 (LRP-1).

5. The in vitro assay system as defined in claim 4, wherein the hepatocyte include cells selected from the group consisting of rodent cell lines AML-12 (ATCC CRL-2254), H2.35 (ATCC CRL-1995), FL83B (ATCC CRL-2390), Fu5AH (Rothblat, 1974), and McA-RH777 (ATCC CRL-1601), human cell lines HepG2 (ATCC HB-8065), HepG2/2.2.1 (ATCC CRL-11997) Hep3B2.1-7 (ATCC HB-8064), C3A (ATCC HB-8065 or ATCC CRL-10741), SK-HEP (ATCC HTB-52), and HuH7 (Creative Bioarray, CSC-C9441L), hepatocytes derived from human induced pluripotent stem cells, and primary cultures of human or mouse hepatocytes.

6. The in vitro assay system as defined in claim 1, wherein the culture medium contains a Chol acceptor.

7. The in vitro assay system as defined in claim 6, wherein the Chol acceptor is a lipid-protein complex, a complex of a lipid with a natural peptide, a complex of a lipid with a synthetic peptide, serum albumin or phospholipid vesicle.

8. The in vitro assay system as defined in claim 1, wherein the culture medium includes a sample of human serum, wherein the human serum is depleted of apolipoprotein B, or wherein the human serum is complete.

9. The in vitro assay system as defined in claim 1, wherein the transporter protein is ABCA1, ABCG1, or SR-BI.

10. An in vitro assay system for measuring cholesterol (Chol) transport, comprising:
   macrophages; and
   hepatocytes;
   the macrophages and the hepatocytes being in a shared culture medium to allow Chol transport between the macrophages and the hepatocytes, wherein the macrophages and the hepatocytes are segregated from each other, wherein the assay system comprises a first and a second culture vessel, wherein the first and second culture vessels are adjacent to each other, wherein a porous membrane is provided between the first and second culture vessels, and wherein the hepatocytes are supported on the membrane, wherein at least one of the macrophages and culture medium includes labeled Chol, wherein the second culture vessel is provided above the first culture vessel, and wherein the macrophages express a transporter protein that mediates Chol efflux from the macrophages into the culture medium, and wherein the Chol exporting cells are pre-treated with an LXR agonist and wherein the macrophages are contained and confined in the first cell culture vessel, the hepatocytes are contained and confined in the second cell culture vessel, and the culture medium permeates the first and second cell culture vessels with the first and second culture vessels in a fluid communication relationship with each other so that the culture medium can diffuse between the first and second cell culture vessels.

11. The in vitro assay system as defined in claim 10, wherein the macrophages include cells selected from the group consisting of a mouse macrophage cell line, a human macrophage cell line, a monocyte-derived cell line, a primary culture of macrophages, a genetically modified macrophage cell line or a macrophage-like cell derived from induced pluripotent stem cells.

12. The in vitro assay system as defined in claim 11, wherein the macrophages include cells selected from the group consisting of murine cell lines J774A.1 (American Type Culture Collection (ATCC) TIB-67), J774.2 (Sigma-Aldrich 85011428), LADMAC (ATCC CRL-2420), RAW 264.7 (ATCC TIB-71), RAW 309 (ATCC TIB-69), P388D1 (ATCC CCL-46), WEHI-265.1 (ATCC TIB-204), and WEHI-274 (ATCC CRL-1679), human cell lines THP-1 (ATCC TIB-202), JM1 (ATCC CRL-10423), KG-1 (ATCC CCL-246), U937 (ATCC CRL-1593.2), AML-193 (ATCC CRL-9589), MD (ATCC CRL-9850), and SC (ATCC CRL-9855), and macrophages derived from tissue resident macrophages, human induced pluripotent stem cells, monocyte cell lines, WEHi cells, THP-1 cells, primary monocytic cells, peripheral blood monocytic cells, CD14$^+$ cells.

13. The in vitro assay system as defined in claim 10, wherein the hepatocytes express a protein that mediates Chol uptake from the culture medium into the hepatocytes, and wherein the protein that mediates Chol uptake from the culture medium into the hepatocytes includes at least one of a low-density lipoprotein receptor (LDLR), scavenger receptor class B, type 1 (SR-B1), CD36 or LDLR-related protein-1 (LRP-1).

14. The in vitro assay system as defined in claim 13, wherein the hepatocyte include cells selected from the group consisting of rodent cell lines AML-12 (ATCC CRL-2254), H2.35 (ATCC CRL-1995), FL83B (ATCC CRL-2390), Fu5AH (Rothblat, 1974), and McA-RH777 (ATCC CRL-1601), human cell lines HepG2 (ATCC HB-8065), HepG2/2.2.1 (ATCC CRL-11997) Hep3B2.1-7 (ATCC HB-8064), C3A (ATCC HB-8065 or ATCC CRL-10741), SK-HEP (ATCC HTB-52), and HuH7 (Creative Bioarray, CSC-C9441 L), hepatocytes derived from human induced pluripotent stem cells, and primary cultures of human or mouse hepatocytes.

15. The in vitro assay system as defined in claim 10, wherein the culture medium contains a Chol acceptor.

16. The in vitro assay system as defined in claim 15, wherein the Chol acceptor is a lipid-protein complex, a complex of a lipid with a natural peptide, a complex of a lipid with a synthetic peptide, serum albumin or phospholipid vesicle.

17. The in vitro assay system as defined in claim 10, wherein the culture medium includes a sample of human serum, wherein the human serum is depleted of apolipoprotein B, or wherein the human serum is complete.

18. The in vitro assay system as defined in claim 10, wherein the transporter protein is ABCA1, ABCG1, or SR-BI.

* * * * *